(12) United States Patent
Fanelli et al.

(10) Patent No.: US 9,145,381 B2
(45) Date of Patent: Sep. 29, 2015

(54) DERIVATIVE OF [(3-HYDROXY-4-PYRON-2-YL)-METHYL]-AMINE AND USE THEREOF AS ANTI-NEOPLASTIC DRUGS

(75) Inventors: Mirco Fanelli, Urbino (IT); Vieri Fusi, Urbino (IT)

(73) Assignee: Universita' Degli Studi Di Urbino (IT)

( * ) Notice: Subject to any disclaimer, the term of this patent is extended or adjusted under 35 U.S.C. 154(b) by 1086 days.

(21) Appl. No.: 13/132,013

(22) PCT Filed: Nov. 27, 2009

(86) PCT No.: PCT/IB2009/007579
§ 371 (c)(1),
(2), (4) Date: Oct. 20, 2011

(87) PCT Pub. No.: WO2010/061282
PCT Pub. Date: Jun. 3, 2010

(65) Prior Publication Data
US 2012/0035255 A1    Feb. 9, 2012

(30) Foreign Application Priority Data
Nov. 28, 2008 (IT) ............... TO2008A0888

(51) Int. Cl.
| | |
|---|---|
| A61K 31/35 | (2006.01) |
| C07D 315/00 | (2006.01) |
| C07D 267/22 | (2006.01) |
| C07D 255/02 | (2006.01) |
| C07D 309/40 | (2006.01) |
| C07D 405/14 | (2006.01) |
| C07D 413/14 | (2006.01) |

(52) U.S. Cl.
CPC ............ C07D 309/40 (2013.01); C07D 405/14 (2013.01); C07D 413/14 (2013.01)

(58) Field of Classification Search
CPC .. C07D 309/40; C07D 413/14; C07D 405/14; C07D 407/12; A61K 31/351; A61P 31/00; A61P 35/00; A61P 35/02

USPC ............ 549/418, 415; 514/459; 540/467, 474
See application file for complete search history.

(56) References Cited

PUBLICATIONS

Badea, F., et al., "Synthesis and Properties of 4N,13N-Bis(3'-hydroxy-6'-methyl-4'-oxo-4H-pyranyl-2'-methylene)-1,7,10,16-tetraoxa-4,13-diazacyclooctadecane", Revue Roumaine de Chimie, 42(1), (1997), 3-9.

(Continued)

*Primary Examiner* — T. Victor Oh
(74) *Attorney, Agent, or Firm* — Schwegman Lundberg & Woessner, P.A.

(57) ABSTRACT

The present invention relates to compounds having general formula (I), i.e. poly-alkyl-bis-maltolic molecules and in particular to derivates of [(3-hydroxy-4-pyron-2-yl)methyl]-amine and pharmaceutically acceptable salts thereof, and to the use thereof as anti-neoplastic drugs, in particular, for the preparation of a medicament for the treatment of neoplastic diseases.

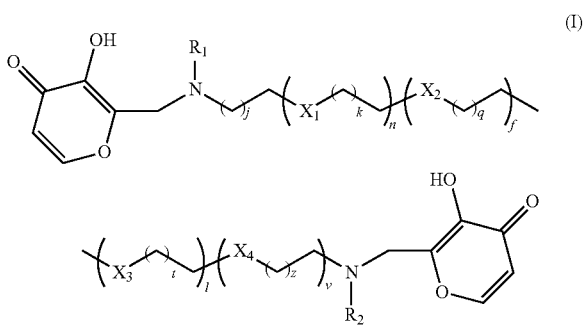

4 Claims, 26 Drawing Sheets

(56) References Cited

PUBLICATIONS

Bransova, J., et al., "Antileukemic activity of 4-pyranone derivatives", Int J Biochem Cell Biol., 27(7), (Jul. 1995), 701-6.

Casero, R. A, et al., "Terminally alkylated polyamine analogues as chemotherapeutic agents", J Med Chem., 44(1), (Jan. 4, 2001), 1-26.

Liang, F., et al., "Medical applications of macrocyclic polyamines", Curr Med Chem., 13(6), (2006), 711-27.

Tenson, T., et al., "The mechanism of action of macrolides, lincosamides and streptogramin B reveals the nascent peptide exit path in the ribosome", J Mol Biol., 330(5), (Jul. 25, 2003), 1005-14.

DERIVATIVE OF [(3-HYDROXY-4-PYRON-2-YL)-METHYL]-AMINE AND USE THEREOF AS ANTI-NEOPLASTIC DRUGS

PRIORITY CLAIM AND RELATED APPLICATIONS

This application is a nationalization under 35 U.S.C. 371 of PCT/IB2009/007579, filed Nov. 27, 2009 and published as WO 2010/061282 A1 on Jun. 3, 2010, which claimed priority under 35 U.S.C. 119 to Italian Patent Office Application No. TO2008A000888, filed Nov. 28, 2008; which applications and publication are incorporated herein by reference in their entirety.

TECHNICAL FIELD

The present invention relates to poly-alkyl-bis-maltolic molecules and in particular to derivates of [(3-hydroxy-4-pyron-2-yl)methyl]-amine and to the use thereof as anti-neoplastic drugs, in particular for the preparation of a medicament for the treatment of neoplastic diseases.

STATE OF THE PRIOR ART

Although great progress has been made in the treatment of neoplastic diseases, the survival of patients affected by tumour remains in many cases very limited (for example, glioblastoma multiforme —GBM, malignant pleural mesothelioma—MPM). The lack of specific therapies, the resistance to currently used chemotherapeutic drugs and the high probability of relapse, represent the main causes for treatment failure in many tumours. In addition, most currently used chemotherapeutic drugs are cytotoxic drugs, the intake of which is known to determine severe side effects. More effective and/or selective drugs are therefore sought for tumour cells.

SUMMARY OF THE INVENTION

A first object of the invention consists in compounds of formula I and pharmaceutically acceptable salts thereof and in the use thereof for the preparation of a medicament.

A further object of the present invention consists in compounds of formula II and pharmaceutically acceptable salts thereof and in the use thereof for the preparation of a medicament.

A further object of the present invention consists in compounds of formula III and pharmaceutically acceptable salts thereof and in the use thereof for the preparation of a medicament.

BRIEF DESCRIPTION OF THE FIGURES

For a better understanding, the present invention is now also described with reference to the accompanying figures, in which:

FIG. 5: Apoptosis induced by L1 after treatment for 72 hours at a concentration of 50 μM. FIGS. 6-13: Effects of L1 on the percentages of the different phases of the cell cycle after a 72 hour treatment at different concentrations. FIG. 14: Apoptosis induced by L9 after a 72 hour treatment at a concentration of 5 μM. FIGS. 15-22: Effects of L9 on the percentages of the different phases of the cell cycle after a 72 hour treatment at different concentrations.

FIG. 24: 500 ng of circular plasmid DNA incubated with maltol, L1, L9 and mechlorethamine (NH2) at the shown concentrations with copper sulphate (CuSO4) for 120 minutes a +37° C. The treatments with ascorbic acid were carried out at concentrations of 50, 100, 150 and 200 μM; FIG. 25: 500 ng of circular plasmid DNA incubated with maltol, L1, L9 without copper sulphate (CuSO4) for 120 minutes at +37° C.; FIG. 26: 100 ng of linear plasmid DNA incubated with L1, L9 and mechlorethamine (NH2) at the concentrations indicated for 30, 60 and 90 minutes at +37° C. NI: non-incubated non-treated control; I: non-treated incubated for 90 minutes.

DETAILED DESCRIPTION OF THE INVENTION

Figure 1:
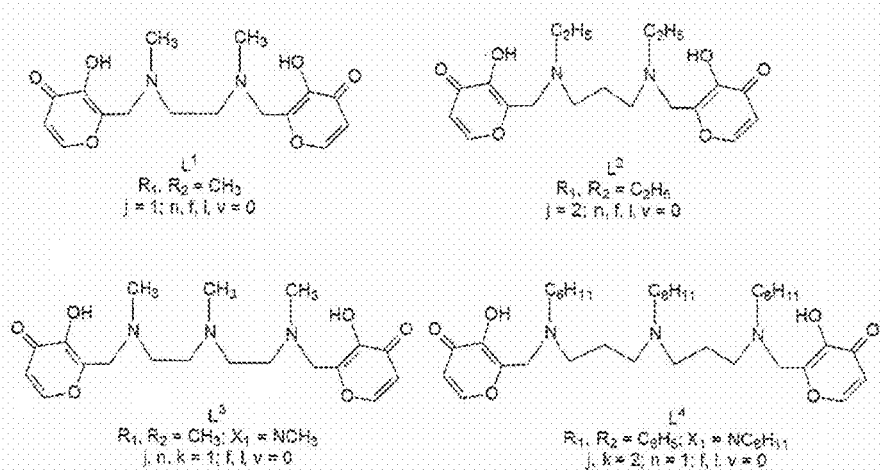
FIG. 1 shows some examples of molecules according to the present invention.
Figure 2:
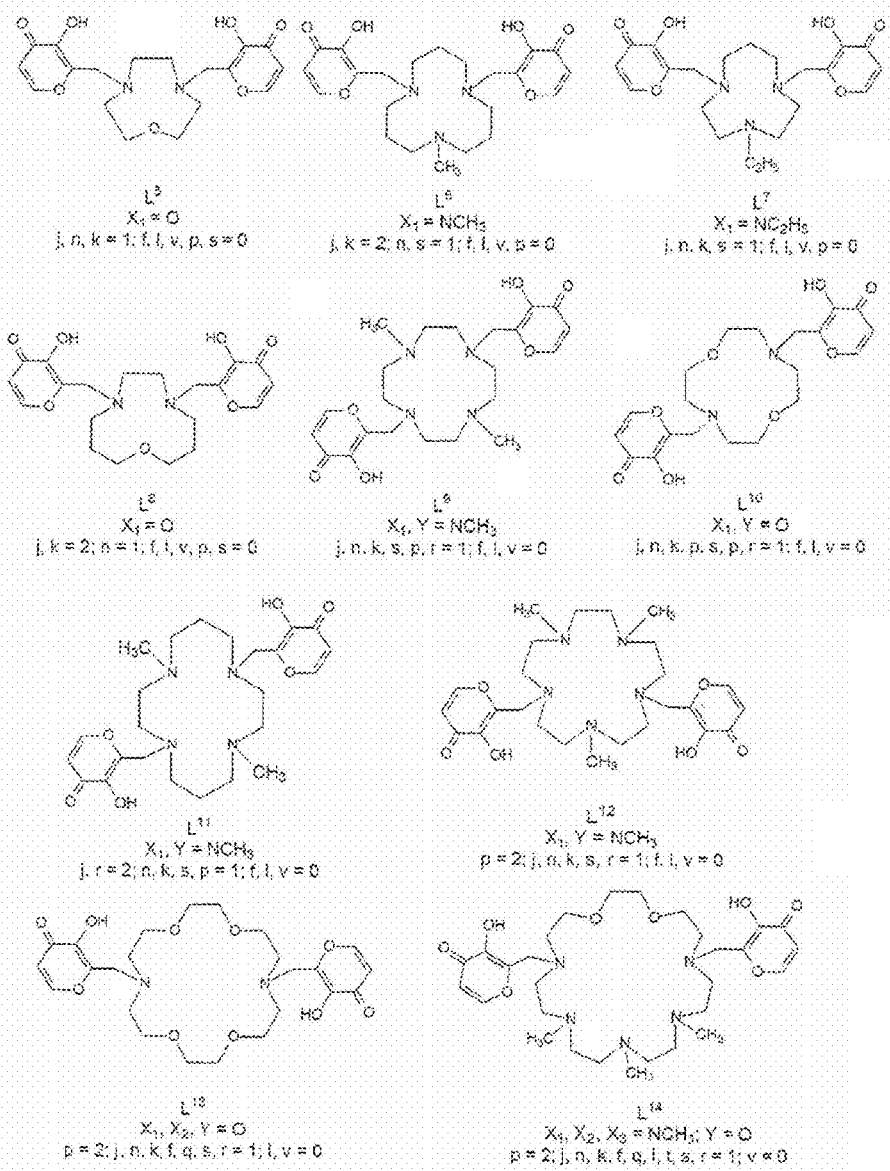
FIG. 2 shows further examples of molecules according to the present invention.

The object of the present invention consists in compounds of formula I:

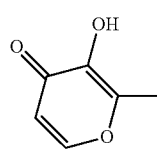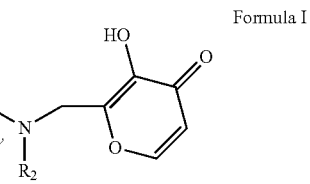

Formula I wherein:
$X_1, X_2, X_3, X_4$=$NR_3$, O
$R_3$=H, $C_mH_{2m+1}$, m=1, 2, 3, 4, 5, 6
n, f, l, v=0,1
k, q, t, z=1, 2
$R_1, R_2$=$C_mH_{2m+1}$, m=1, 2, 3, 4, 5, 6 or alternatively form a ring and have the following meaning:

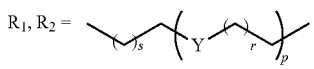

wherein:
Y=NR$_3$, O
R$_3$=H, C$_m$H$_{2m+1}$, m=1, 2, 3, 4, 5, 6
p=0, 1, 2, 3, 4;
s=0, 1, 2
r=1, 2
and pharmaceutically acceptable salts thereof.

The compounds of formula II are preferred:

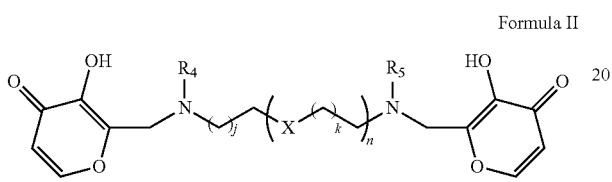

Formula II wherein:
X=NR$_3$, O
R$_3$=H, m=1, 2, 3, 4, 5, 6
n=0, 1, 2, 3, 4
j, k=1, 2
R$_4$, R$_5$=C$_m$H$_{2m+1}$, m=1, 2, 3, 4, 5, 6.

The compounds of formula III are also preferred:

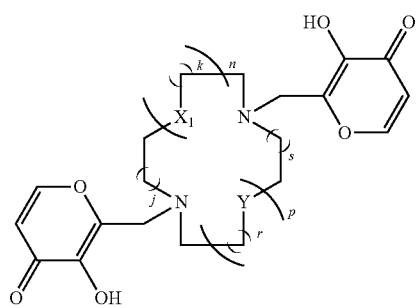

wherein:
X$_1$, Y=NR$_3$, O
R$_3$=H, C$_m$H$_{2m+1}$, m=1, 2, 3, 4, 5, 6
n=0, 1, 2, 3
j, s=0, 1, 2
p=0, 1, 2, 3
r, k=1, 2
and pharmaceutically acceptable salts thereof.

Among the compounds of formula I, examples of C1-C6 aliphatic R3 substituents are methyl, ethyl, propyl, isopropyl, butyl, sec-butyl, ter-butyl, pentyl and hexyl.

Among the compounds of formula II, preferred compounds are those in which X is N—CH$_3$, and n is 0 or 1.

Among the compounds of formula III, preferred compounds are those in which X$_1$ and Y are NH, N-methyl, and N-ethyl or alternatively in which X or Y are O so as to obtain poly-oxa-aza crown ether compounds. The parameters n, p may be modulated by inserting multiple ethers with amine groups thus obtaining compounds even having 8 functional groups. The parameters j, k, may be varied with the aim of separating these functions with ethyl or propyl aliphatic chains. By varying many parameters, the size of the ring may be modulated from smaller substituted 1,4,7-cyclononanes.

Among the compounds of formula III, a first group of preferred compounds comprises those based on macrocycles of cyclodecanes in which X and Y are N—CH3 or O, and n=k=j=p=s=r=1 (all ethylic chains).

The person skilled in the art is capable of synthesising and characterising all of the compounds of formula I, II, III, by performing the appropriate substitutions of the various groups.

The pharmaceutically acceptable salts are all organic and inorganic salts that can salify the basic centres which occur and have no toxic effect or other undesired effects.

The following compounds are particularly preferred:

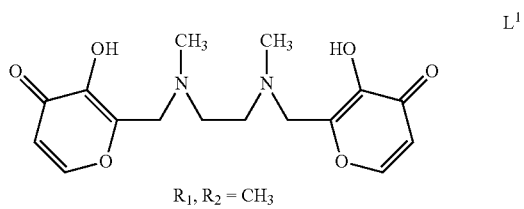

R$_1$, R$_2$ = CH$_3$
j = 1; n, f, l, v = 0

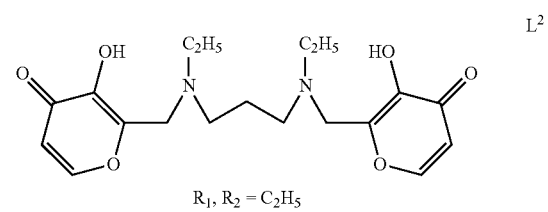

R$_1$, R$_2$ = C$_2$H$_5$
j = 2; n, f, l, v = 0

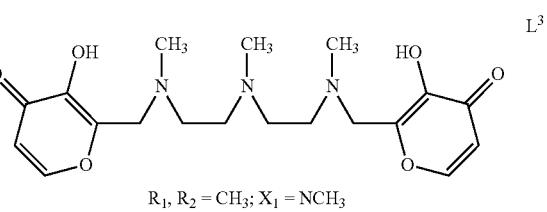

R$_1$, R$_2$ = CH$_3$; X$_1$ = NCH$_3$
j, n, k = 1; f, l, v = 0

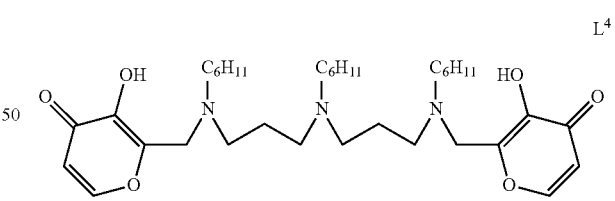

R$_1$, R$_2$ = C$_6$H$_5$; X$_1$ = NC$_6$H$_{11}$
j, k = 2; n = 1; f, l, v = 0

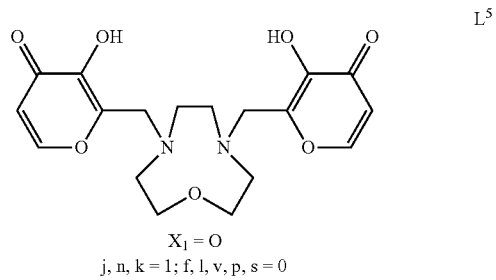

X$_1$ = O
j, n, k = 1; f, l, v, p, s = 0

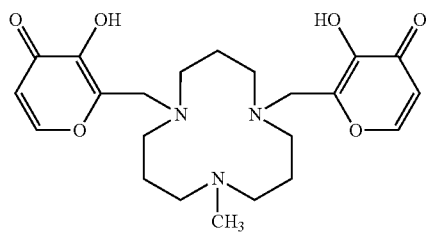
$X_1 = NCH_3$
j, k = 2; n, s = 1; f, l, v, p = 0
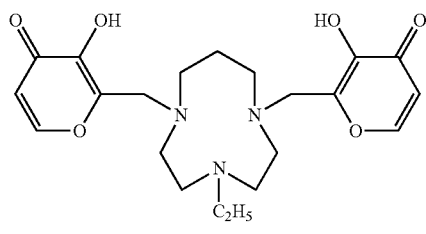
$X_1 = NC_2H_5$
j, n, k, s = 1; f, l, v, p = 0
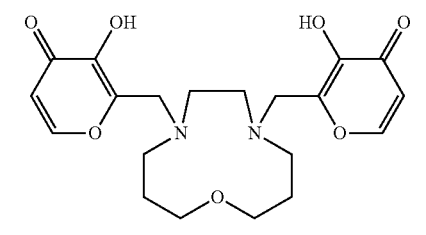
$X_1 = O$
j, k = 2; n = 1; f, l, v, p, s = 0
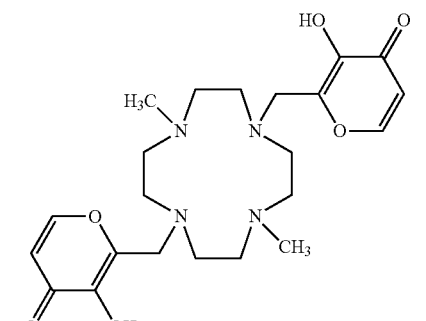
$X_1, Y = NCH_3$
j, n, k, s, p, r = 1; f, l, v = 0
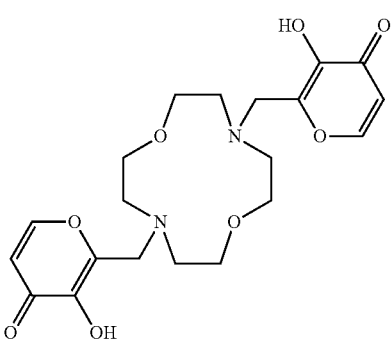
$X_1, Y = O$
j, n, k, p, s, p, r = 1; f, l, v = 0
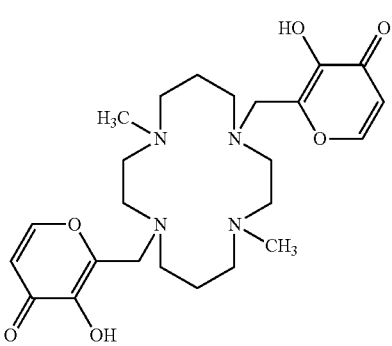
$X_1, Y = NCH_3$
j, r = 2; n, k, s, p = 1; f, l, v = 0
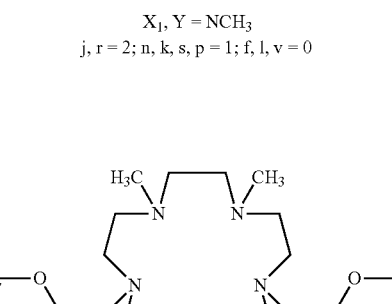
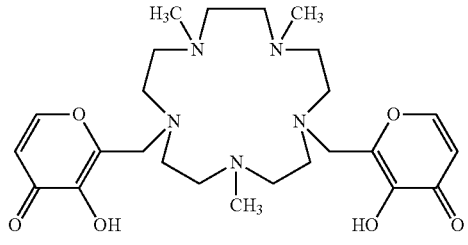
$X_1, Y = NCH_3$
p = 2; j, n, k, s, r = 1; f, l, v = 0
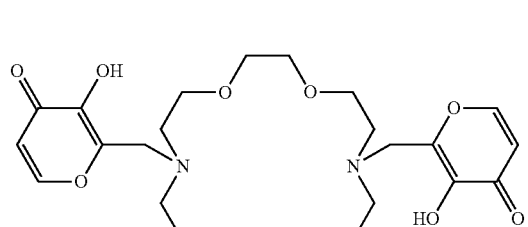
$X_1, X_2, Y = O$
p = 2; j, n, k, f, q, s, r = 1; l, v = 0

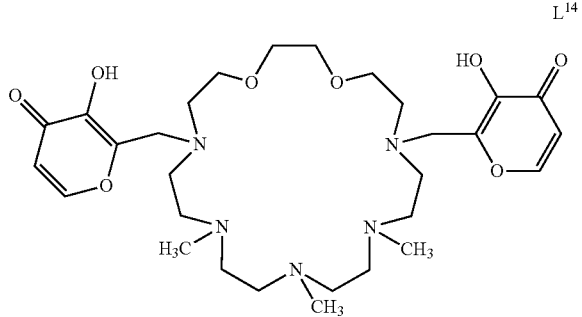

$L^{14}$ $X_1, X_2, X_3 = NCH_3; Y = O$
$p = 2; j, n, k, f, q, l, t, s, r = 1; v = 0$

Furthermore, especially preferred compounds are —N,N'-bis[(3-hydroxy-4-pyron-2-yl)methyl]-N,N'-dimethylethyl-endiamine ($L^1$) and
4(N),10(N)-bis[(3-hydroxy-4-pyron-2-yl)methyl]-1,7-dimethyl-1,4,7,10-tetraazacyclododecane ($L^9$).

As specific example of the present invention, the following compounds, N,N'-bis[(3-hydroxy-4-pyron-2-yl)methyl]-N,N'-dimethylethylendiamine ($L^1$) and 4(N),10(N)-bis[(3-hydroxy-4-pyron-2-yl)methyl]-1,7-dimethyl-1,4,7,10-tetraazacyclododecane ($L^9$), have shown a cytotoxic activity against different neoplastic models.

All of the compounds have a [(3-hydroxy-4-pyron-2-yl)methyl]-amine unit also referred to as "MALT". The MALT units are separated by different aliphatic spacers which may or may not have a cyclic backbone.

All of the classes of compounds I, II and III, by mere way of example, may be prepared following a synthetic approach similar to that disclosed in Scheme 1.

The synthetic procedure includes the coupling of a reagent (a), appropriately activated and protected, with a secondary amine present in reagent (b) or (e); protected products (c) or (f), both containing MALT functions, may therefore respectively be obtained. The deprotection of the hydroxyl function of the maltolic units allows to obtain the desired compounds (d) or (g). Reagent (a) is obtained from the commercial compound 2-methyl-3-hydroxy-4-pyrone (maltol), which is protected or activated for coupling by methods disclosed in literature. Reagents (b) and (e) containing two secondary amine groups, in order to react with two equivalents of (a), are synthesised by following standard procedures known in the literature.

The synthetic schemes which lead to the preparation of compounds referred to as L1 and L9 are shown in Schemes 2 and 3 only by way of example.

Scheme 1

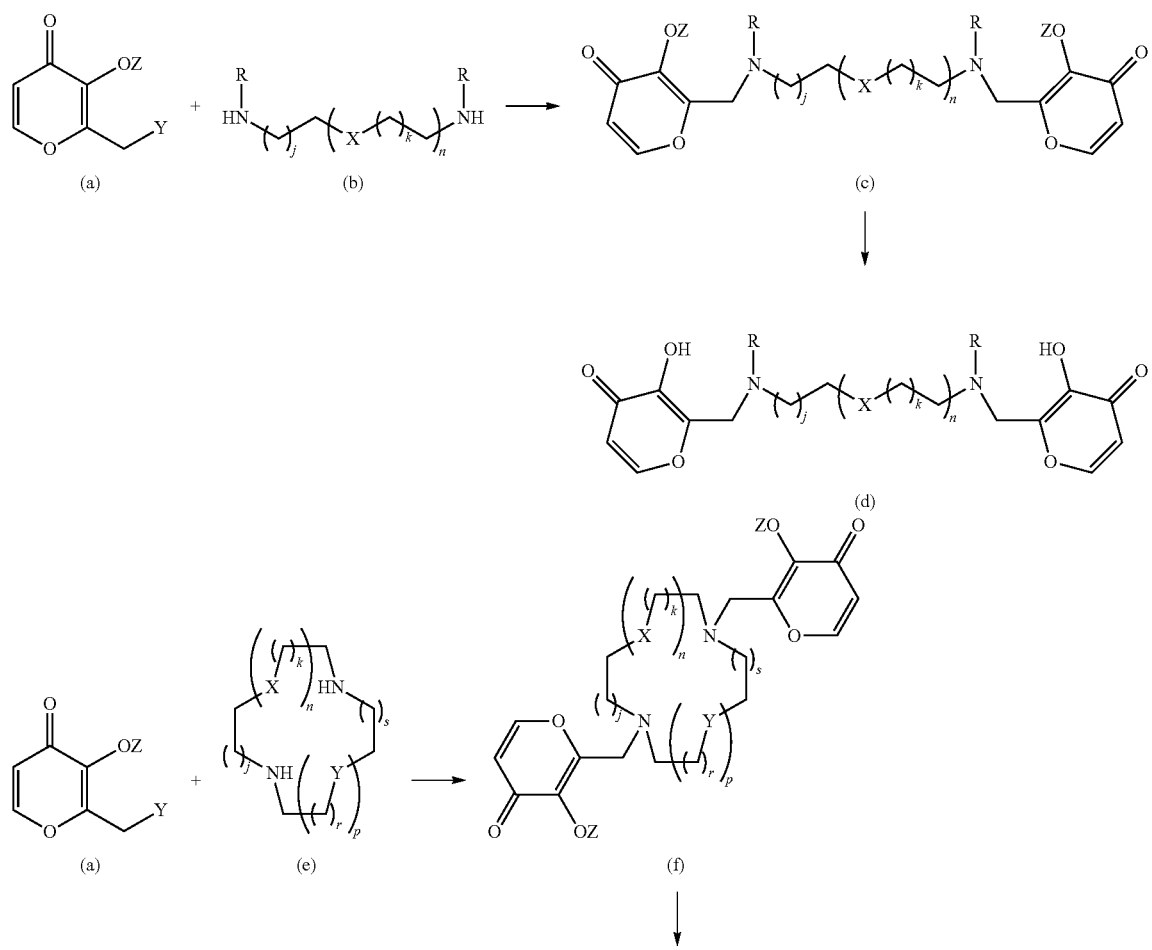

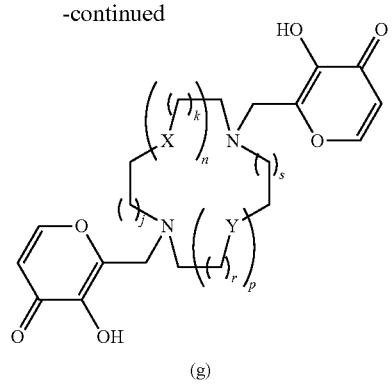

(g)

Scheme 2

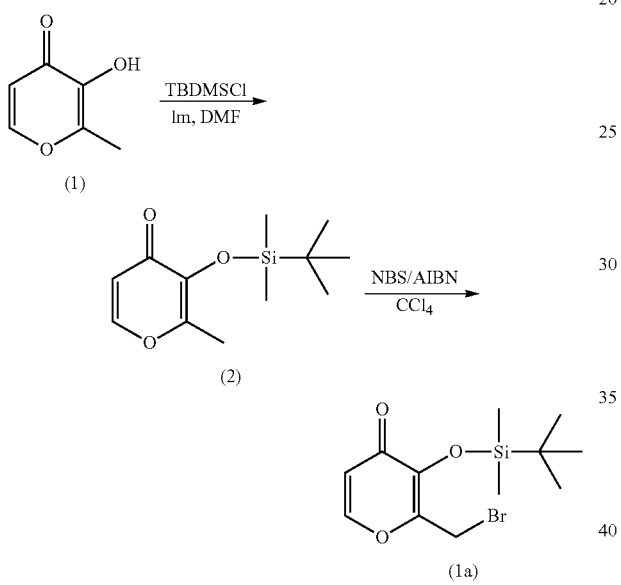

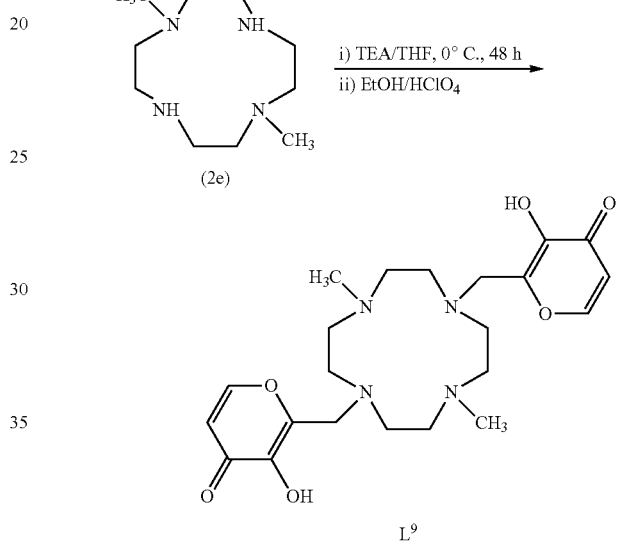

Scheme 3

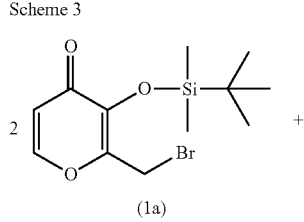

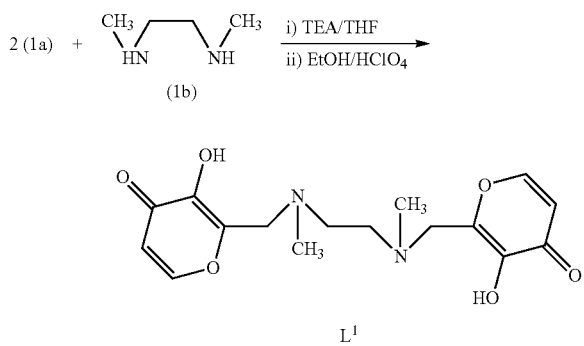

The compounds of formula I, II and III have shown to be effective as they alter the structure of chromatin in cell-free assays and induce important biological responses in different tumour cell populations, in particular impairment of the cell cycle and programmed cell death.

In the compounds of formula II, the compounds have two MALT units separated by linear polyalkylamine or polyalkyloxa chains.

In the compounds of formula III, two MALT units are separated by a cyclic spacer included in the class of the poly-aza-crown or poly-oxa-aza-crown ethers.

The compounds of the present invention and the pharmaceutically acceptable salts thereof may be used as pharmaceutical compositions together with pharmaceutically acceptable carriers, stabilisers, diluents or excipients.

The compounds and the corresponding pharmaceutical compositions may be used for the preparation of a medicament.

The use as an antibiotic or for the preparation of a medicament for the treatment of tumours is especially advantageous.

The use for the preparation of a medicament for inhibiting the proliferation of neoplastic cells, in particular for the preparation of a medicament for inducing the differentiation of tumour cells in a tumour is especially preferred.

Even more advantageously the compounds are used for the treatment of primary or secondary tumours, for example rhabdomyosarcoma or haemopoietic tumours, in particular leukaemias and lymphomas.

The examples of preparation of the following compounds further disclose the invention, without limiting the scope thereof.

Example 1

Preparation of 3-(tert-butyl-dimethylsilyl)oxy-2-methyl-4-pyrone

A solution of imidazole (Im, 5.45 g, 0.08 mol) in N,N-dimethylformamide (20 ml) is added in an inert atmosphere and dropwise to a solution containing 3-hydroxy-2-methyl-4-pyrone (5.00 g, 0.04 mol) and tert-butyl-dimethylchlorosilane (TBDMSCl, 7.00 g, 0.044 mol) in N,N-dimethylformamide (100 ml). The mixture obtained thereby is maintained stirring at a room temperature for 6 h and then diluted by adding a 5% hydrogen carbonate aqueous solution (150 ml). The mixture obtained thereby is extracted with hexane (6×50 ml); the extracted organic phases are combined, anhydrified on sodium sulphate, and evaporated under vacuum obtaining the desired 3-(tert-butyl-dimethylsilyl)oxy-2-methyl-4-pyrone compound as a colourless crystalline solid (9.61 g).

Yield: 98%

1H-NMR (200 MHz, 25° C., CDCl3, ppm): 7.58 (d, 1H, J=5.56 Hz), 6.29 (d, 1H, J=5.56 Hz), 2.31 (s, 3H), 0.96 (s, 9H), 0.26 (s, 6H)

13C-NMR (200 MHz, 25° C., CDCl3, ppm): 3.8, 14.8, 18.7, 25.9, 115.5, 142.8, 152.8, 154.6, 174.0.

Example 2

Preparation of N,N'-bis[(3-hydroxy-4-pyron-2-yl)methyl]-N,N'-dimethylethylendiamine dihydroperchlorate (L1.2HClO4)

α,α'-azoisobutyrronitrile (AIBN, 0.33 g, 0.002 mol) is added in an inert atmosphere to a reflux and stirred solution of 3-(tert-butyl-dimethylsilyl)oxy-2-methyl-4-pyrone (3.5 g, 0.015 mol) and N-bromosuccinimide (NBS, 3.0 g, 0.016 mol) in carbon tetrachloride (70 ml).

The resulting mixture is maintained stirring and with reflux for 1 h testing it with TLC on silica gel (hexane/ethyl acetate 1:1 eluent; Rf=0.85); the mixture is subsequently cooled at a room temperature and then filtered. The resulting yellow solution contains compound 1a and is used without further purification by adding it dropwise in an inert atmosphere at 0° C. to a solution of N,N'-dimethylamine (1b, 0.45 g, 0.005 mol) and triethylamine (TEA, 2.12 ml, 0.015 mol) in THF (70 ml). The reaction mixture is maintained stirring at 0° C. for 48 h and then filtered resulting in a red-orange solution which is coevaporated under vacuum several times with ethanol (3×100 ml). The resulting red oil residue is dissolved in ethanol (50 ml) and the resulting solution is added dropwise to a 10% perchloric acid solution in ethanol up to total precipitation of a solid yellow. The resulting solid is filtered, washed with ethanol, and recrystallised by sodium perchlorate saturated water obtaining L1.2HClO4 as a white solid (1.67 g).

Yield: 58%

1H-NMR (200 MHz, 25° C., D2O pH=2, ppm): 7.99 (d, 2H, J=5.55 Hz), 6.48 (d, 2H, J=5.55 Hz), 4.43 (s, 4H), 3.61 (s, 4H), 2.87 (s, 6H);

13C-NMR (200 MHz, 25° C., D2O pH=2, ppm): 175.5, 157.2, 146.6, 140.9, 114.1, 52.2, 49.5, 40.9.

MS (m/z): 337.3 (M+H)

Analysis calculated for: C16H22C12N2O14(%): C, 32.76; H, 4.32; N, 5.46. Found (%): C, 32.8; H, 4.3; N, 5.5.

Example 3

Preparation of 4(N),10(N)-bis[(3-hydroxy-4-pyron-2-yl)methyl]-1,7-dimethyl-1,4,7,10-tetraazacyclododecane tetrahydroperchlorate (L9.3HClO4.H2O).

Compound 1a is prepared as previously disclosed from α,α'-azoisobutyrronitrile (AIBN, 0.33 g, 0.002 mol), 3-(tert-butyl-dimethylsilyl)oxy-2-methyl-4-pyrone (3.5 g, 0.015 mol) and N-bromosuccinimide (NBS, 3.0 g, 0.016 mol) in carbon tetrachloride and used immediately without further purification. 1a is added at 0° C. dropwise in an inert atmosphere to a solution of 1,7-dimethyl-1,4,7,10-tetraazacyclododecane (2e, 1.00 g, 0.005 mol) and triethylamine (TEA, 2.12 ml, 0.015 mol) in THF (70 ml). The reaction mixture is maintained stirring at 0° C. for 12 h, then coevaporated under vacuum with ethanol (3×100 ml). The resulting residue is a red oil which is solubilised in ethanol (50 ml); the resulting solution is added to a 10% perchloric acid solution in ethanol up to total precipitation of a white solid which is filtered, washed with ethanol and recrystallised by sodium perchlorate saturated water obtaining L9.3HClO4.H2O as a white solid (1.69 g).

Yield: 44%

1H-NMR (200 MHz, 25° C., D2O pH=2, ppm): 7.97 (d, 2H, J=5.50 Hz), 6.44 (d, 2H, J=5.50 Hz), 3.89 (s, 4H), 3.54 (m, 8H), 2.95 (m, 8H), 2.88 (s, 6H);

13C-NMR (200 MHz, 25° C., D2O pH=2, ppm): 175.4, 157.1, 149.8, 144.7, 114.0, 53.5, 49.0, 47.2, 42.4.

MS (m/z): 449.5 (M+H)

Analysis calculated for C22H37C13N4O19(%): C, 34.41; H, 4.86; N, 7.30. Found (%): C, 34.4; H, 4.8; N, 7.4.

Example 4

Evaluation of the Antiproliferative Activity in Different Tumour Cell Lines

In order to evaluate the ability of these compounds to inhibit the proliferation of tumour cells in vitro, eight cell lines were selected, four deriving from haematopoietic tumours and four deriving from solid tumours. The tested hematopoietic lines comprise three myeloid tumour cell lines (U937—acute monocytic leukaemia, NB4—acute promyelocytic leukaemia, HL-60—acute myeloid leukaemia) and a lymphoid tumour cell line (JURKAT—T cell leukaemia), while cell lines deriving from multiform glioblastoma (U-373MG), from uterine cervix cancer (HeLa), from malignant pleural mesothelioma (H-28) and from rhabdomyosarcoma (RH-4) have been used as lines representative of solid tumours. Each cell line has been grown in the appropriate growth medium at 37° C. (RPMI 1640 for the hematopoietic lines and DMEM for the adhering cells deriving from solid tumours—Cambrex, Walkersville, Md., USA) added with 10% FBS, 1% glutamine, 100 IU/ml penicillin, 100 µg/ml streptomycin in a highly humidified atmosphere at 5% CO2. The hematopoietic populations were diluted with preheated growth medium at 37° C. at a concentration of 1×10$^5$ cells/ml and aliquots of 2 ml were aliquoted in each single well of 6-well plates. The adhering cells were trypsinized, diluted with preheated growth medium at 37° C. and $0.5\times10^5$ cells were aliquoted in each single well of 6-well plates. The cells in an exponential growth phase were treated with different concentrations of L1 or L9. Both compounds were diluted in distilled water and the treatments were repeated every 24 hours. 72 hours after starting the treatments, cell viability was evaluated by means of Trypan blue staining and the inhibiting concentration (IC50) was computed for each cell line as the concentration allowing to reduce by 50% the number of viable cells, with respect to a non-treated control.

Figure 3:
FIGS. 3 and 4 show a diagram with the inhibiting concentrations (IC50) of L1 (FIG. 3) and L9 (FIG. 4) in different tumour cell lines. Cells in an exponential growth phase were treated for 72 hours with L1 and L9 and then harvested and stained with Trypan blue in order to determine viability. The values of IC50 have been computed for each compound as the concentration that can determine a 50% reduction in viable cells with respect to a non-treated control.
Figure 4:
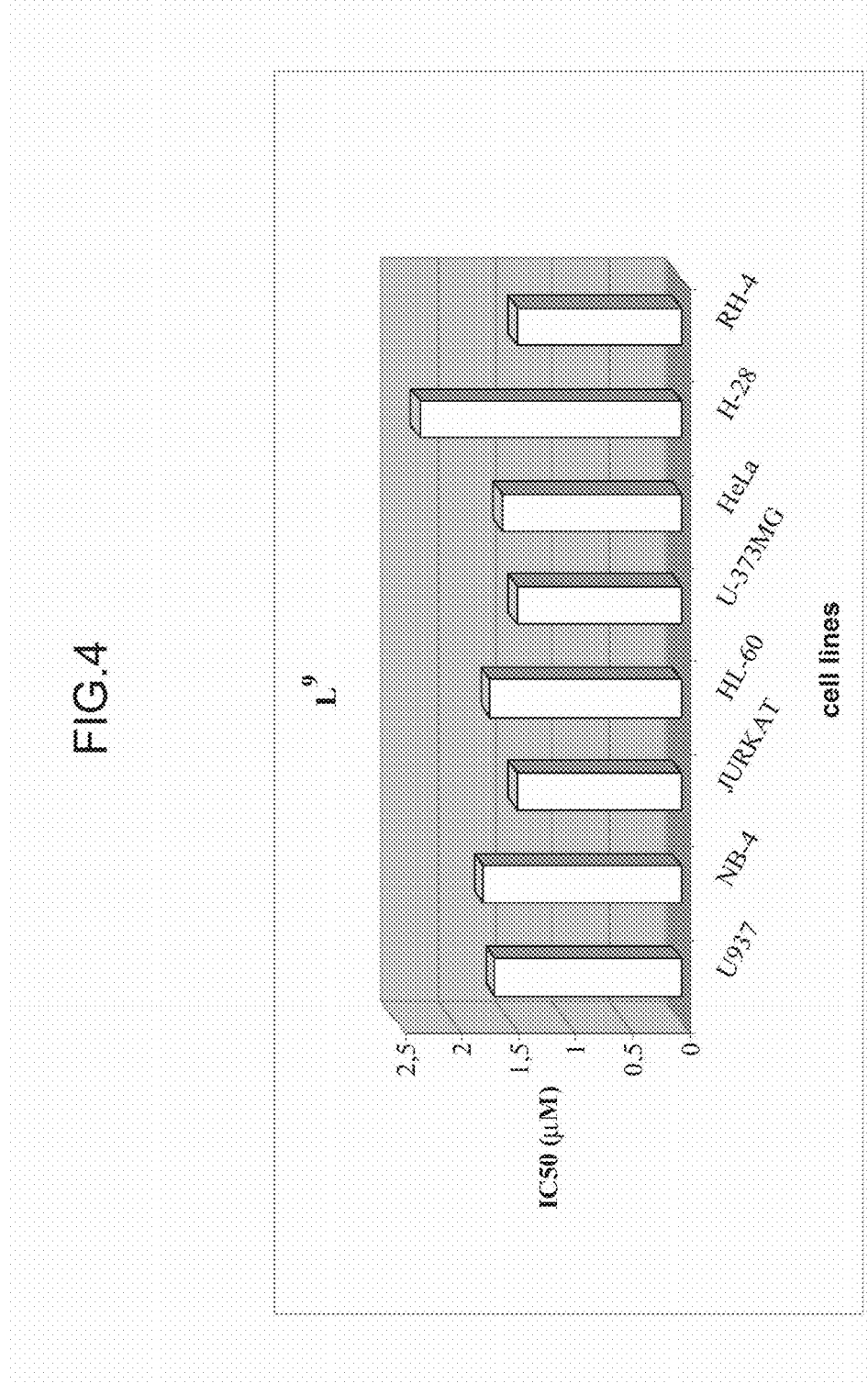

Micromolar concentrations of these new compounds determine a strong reduction of the number of viable cells in all of the tested cell lines. Compound L1 displayed a strong selectivity for some cell lines, as the IC50 values of this molecule vary from a minimum of 4.49 μM in RH-4 cells to a maximum of 30.47 μM in HeLa cells (FIG. 3A). Furthermore, this compound appears to have a certain specificity for hematopoietic cells (average of the IC50 values: 10.44 μM) with respect to those deriving from solid tumours (IC50 mean: 21.99 μM). On the contrary, the IC50 values of L9 show very small variations in the different tested cell lines although this molecule has an antiproliferative activity at definitely lower concentrations (from 1.45 μM to 2.31 μM—FIG. 3B).

Example 5

Analysis of the Alterations of the Cell Cycle and of the Induction of Programmed Cell Death (Apoptosis)

The effects of L1 and L9 on the progression of the cell cycle and on its hypothetical ability to induce the apoptotic process were evaluated by cytofluorimetric analysis by means of propidium iodide staining of all of the previously tested cell lines. Cell treated with different concentrations of the two compounds, as previously disclosed, have been harvested and washed with cold phosphate buffer (1×PBS). The cells were resuspended in cold 70% ethanol and fixed at +4° C. for 24 hours. All of the samples were then centrifuged at 1300 rpm at +4° C. for 3 minutes and then resuspended in a solution containing propidium iodide (1×PBS; 0.1% Triton X-100, 0.1% sodium citrate, 250 μg/ml RNasi A, 50 μg/ml propidium iodide) and, after 24 hours of incubation at +4° C., a minimum of $1\times10^4$ events were acquired at the BD FACScan cytofluorimeter (BD Biosciences, San Jose, Calif., USA). The acquisitions were analysed by a FlowJo 5.7.2 software (Tree Star, Inc., Ashland, Oreg., USA) in order to determine the percentage of cells in different phases of the cell cycle and displaying hypoploid conditions (Apoptotic cells). The induction of programmed cell death was computed as the difference between the percentage of hypodiploid cells in treated and non-treated samples.

Figure 14:
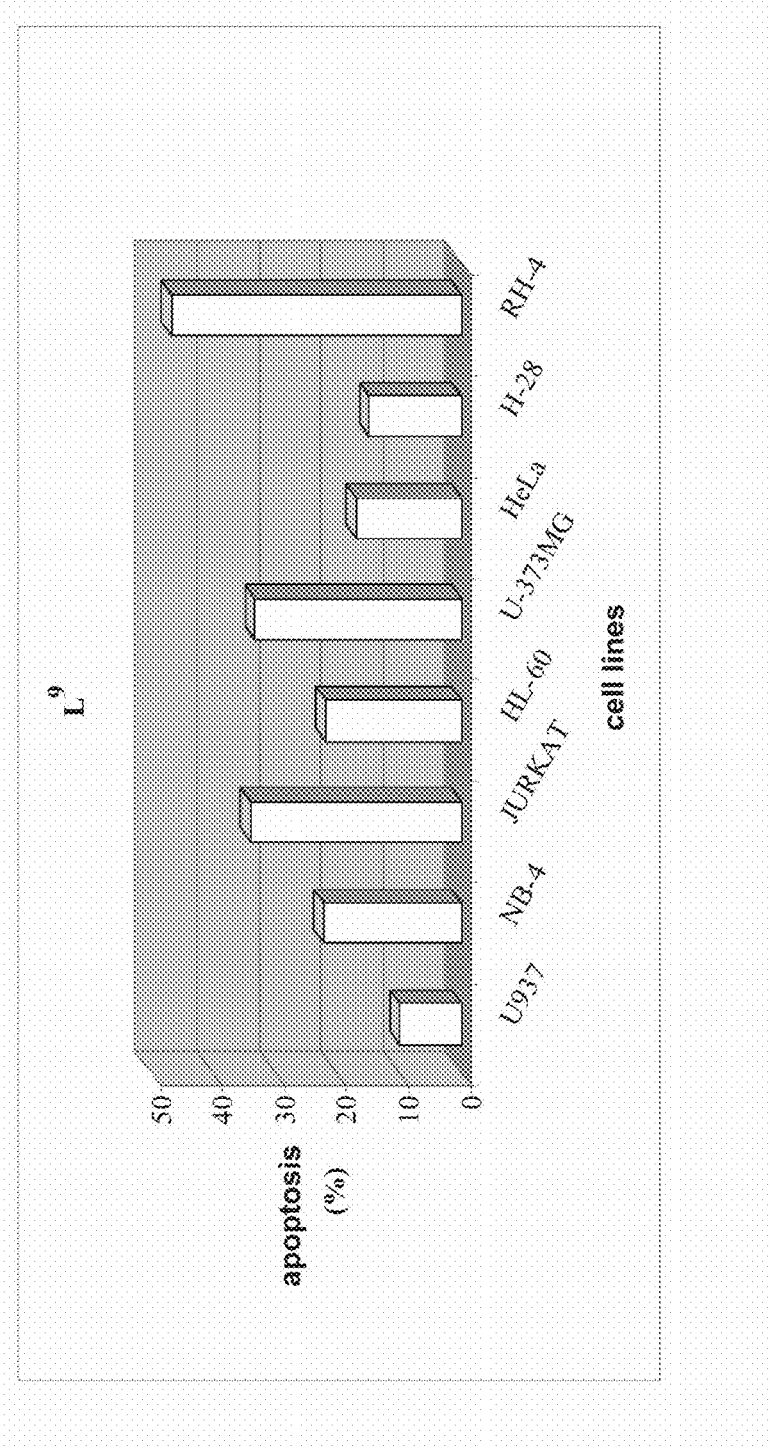
Figure 15:
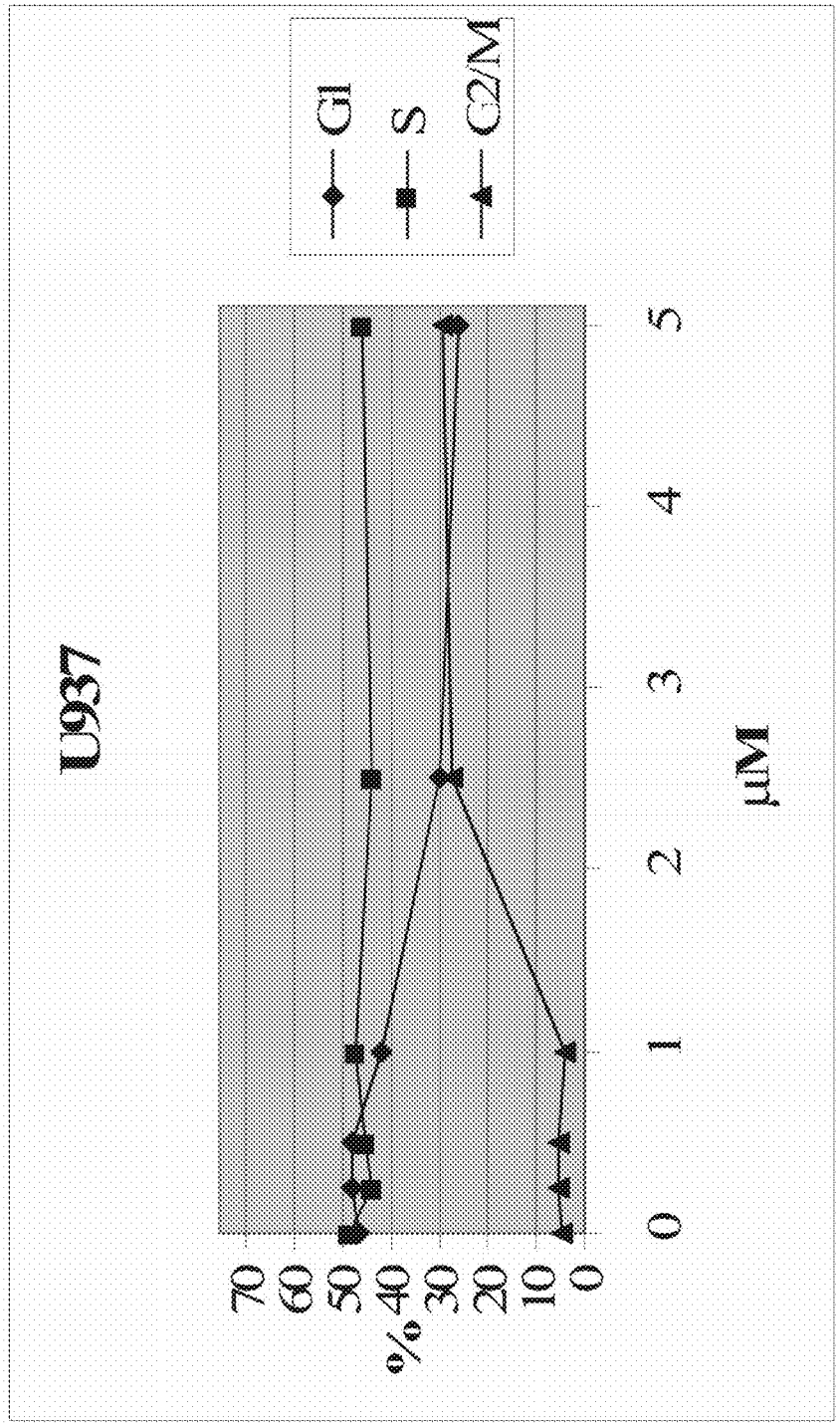
Figure 16:
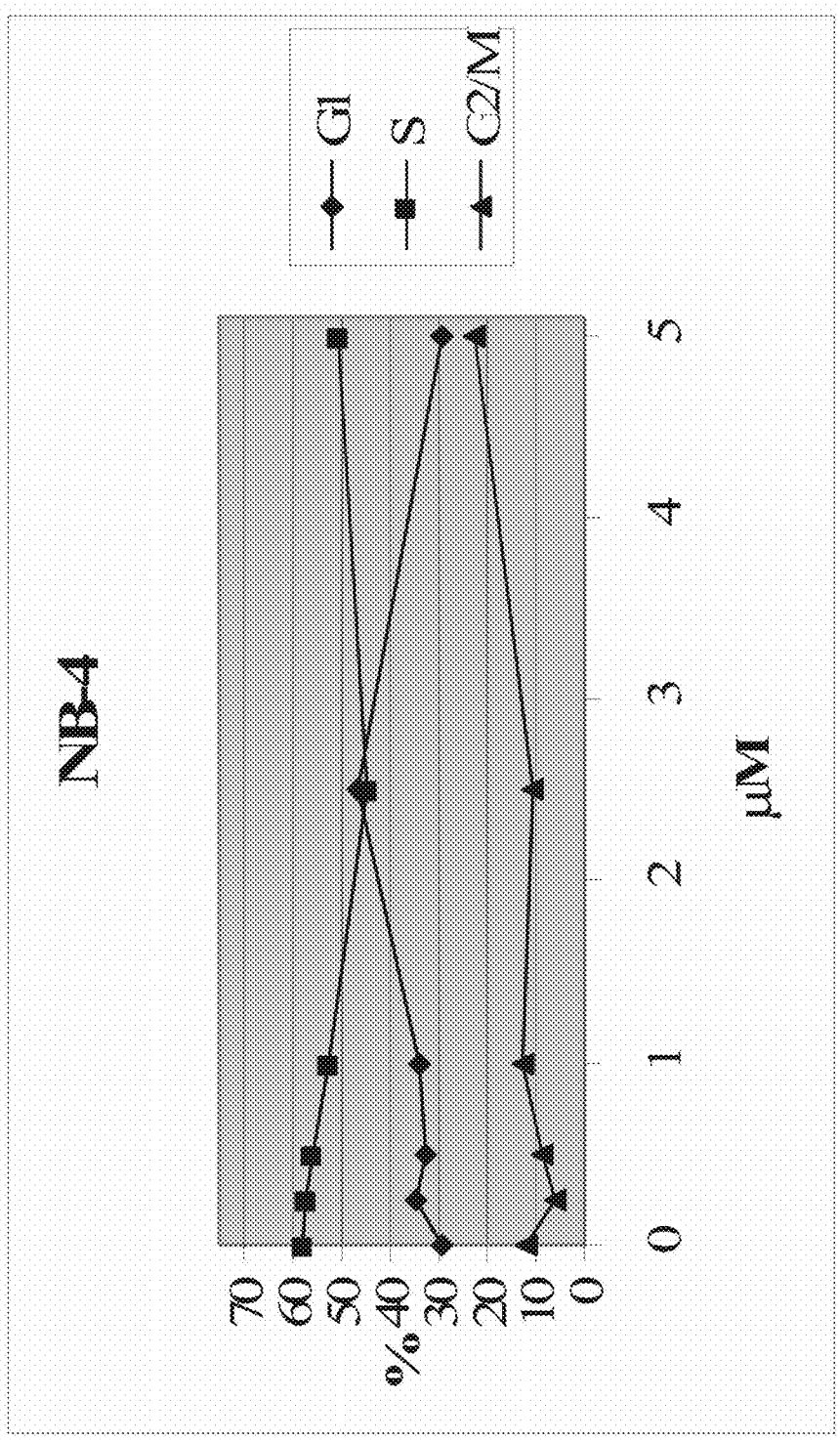
Figure 17:
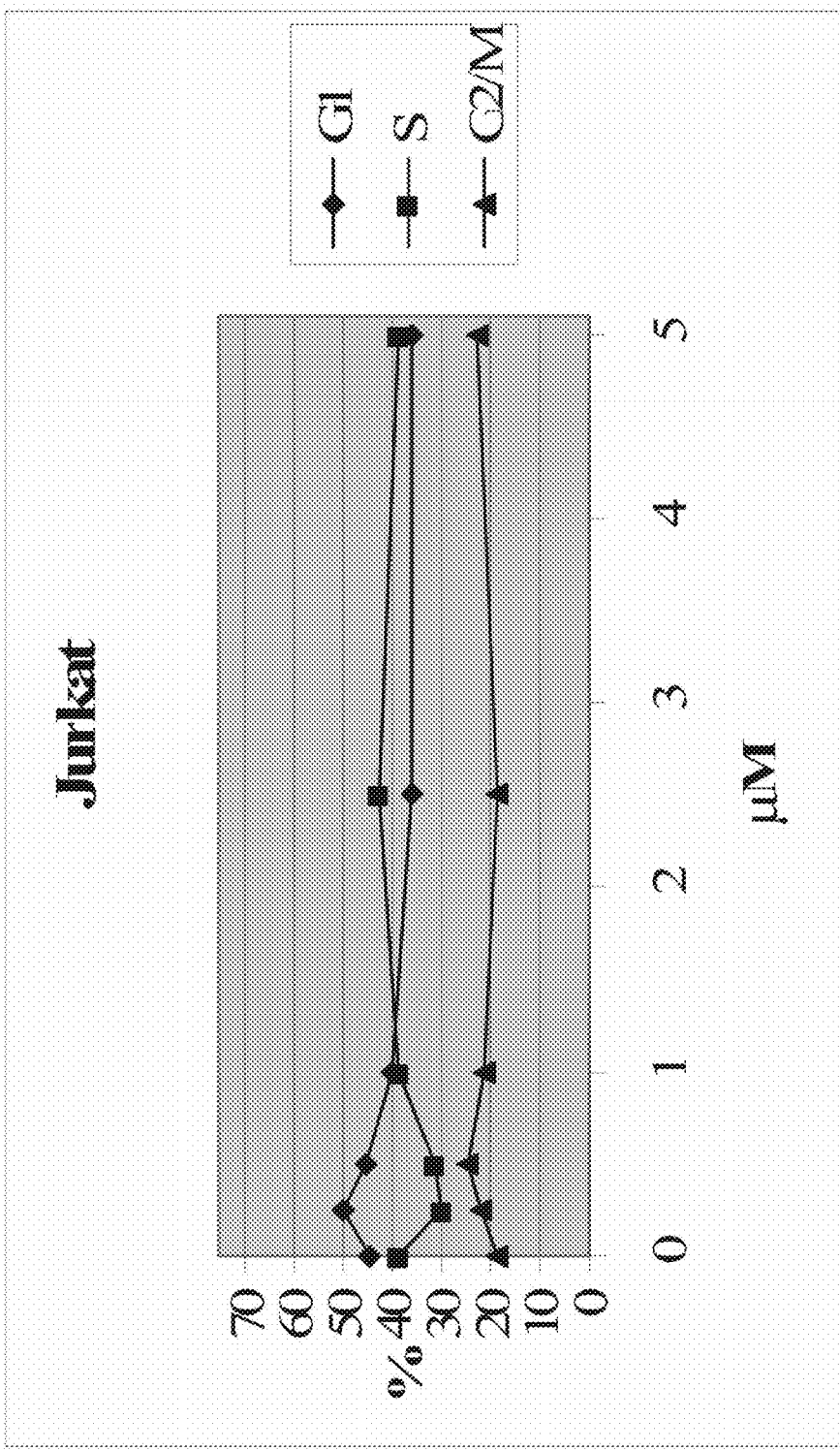
Figure 18:
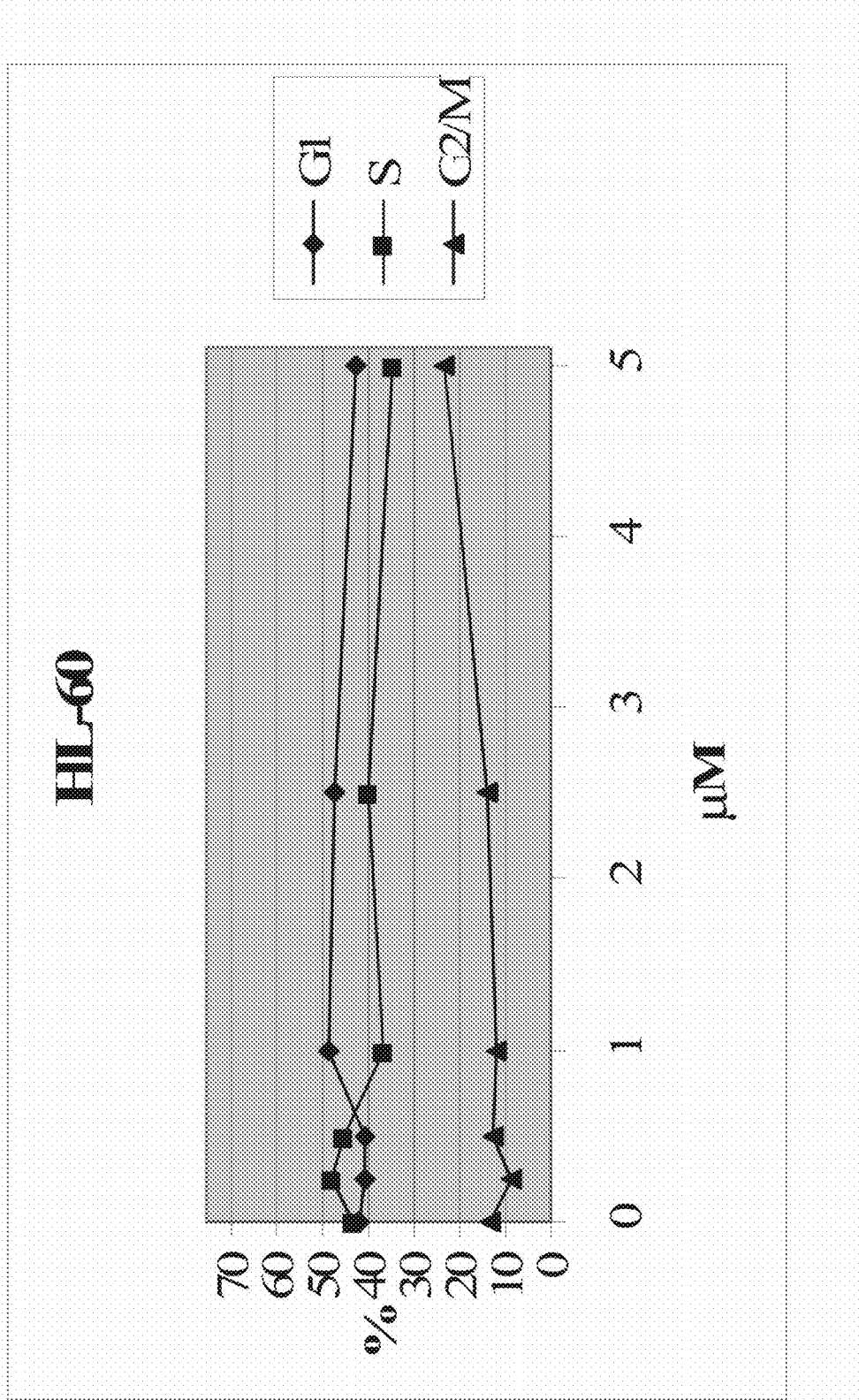
Figure 19:
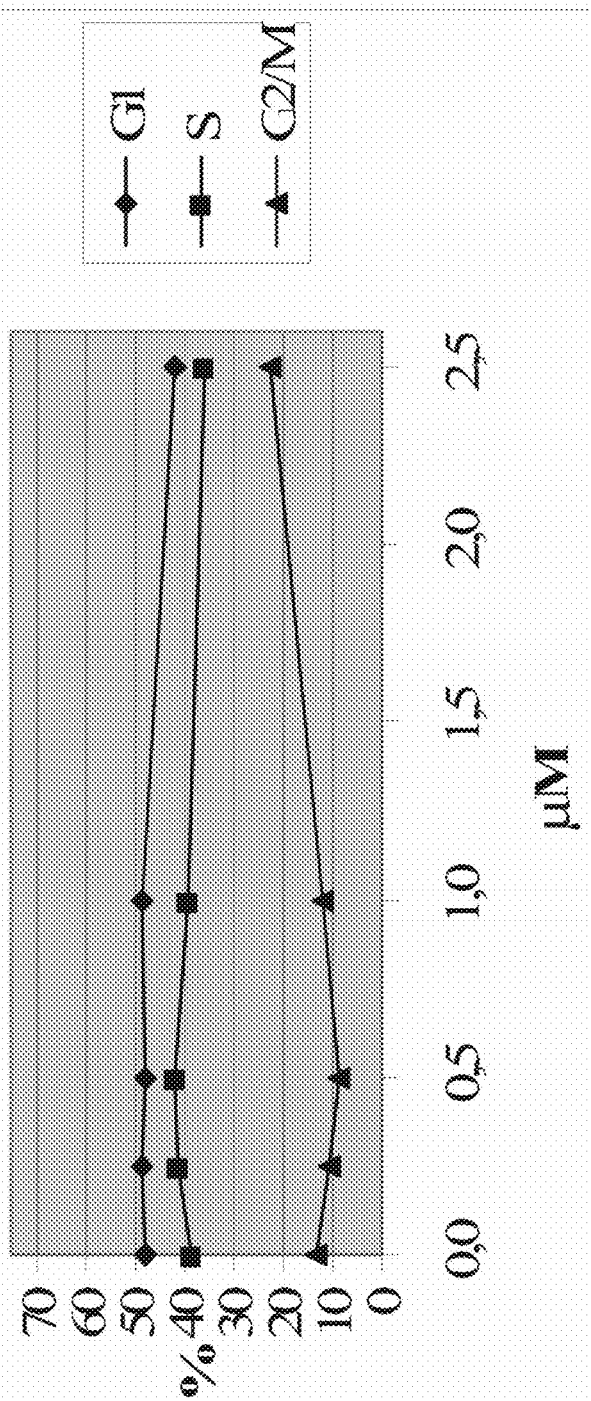
Figure 20:
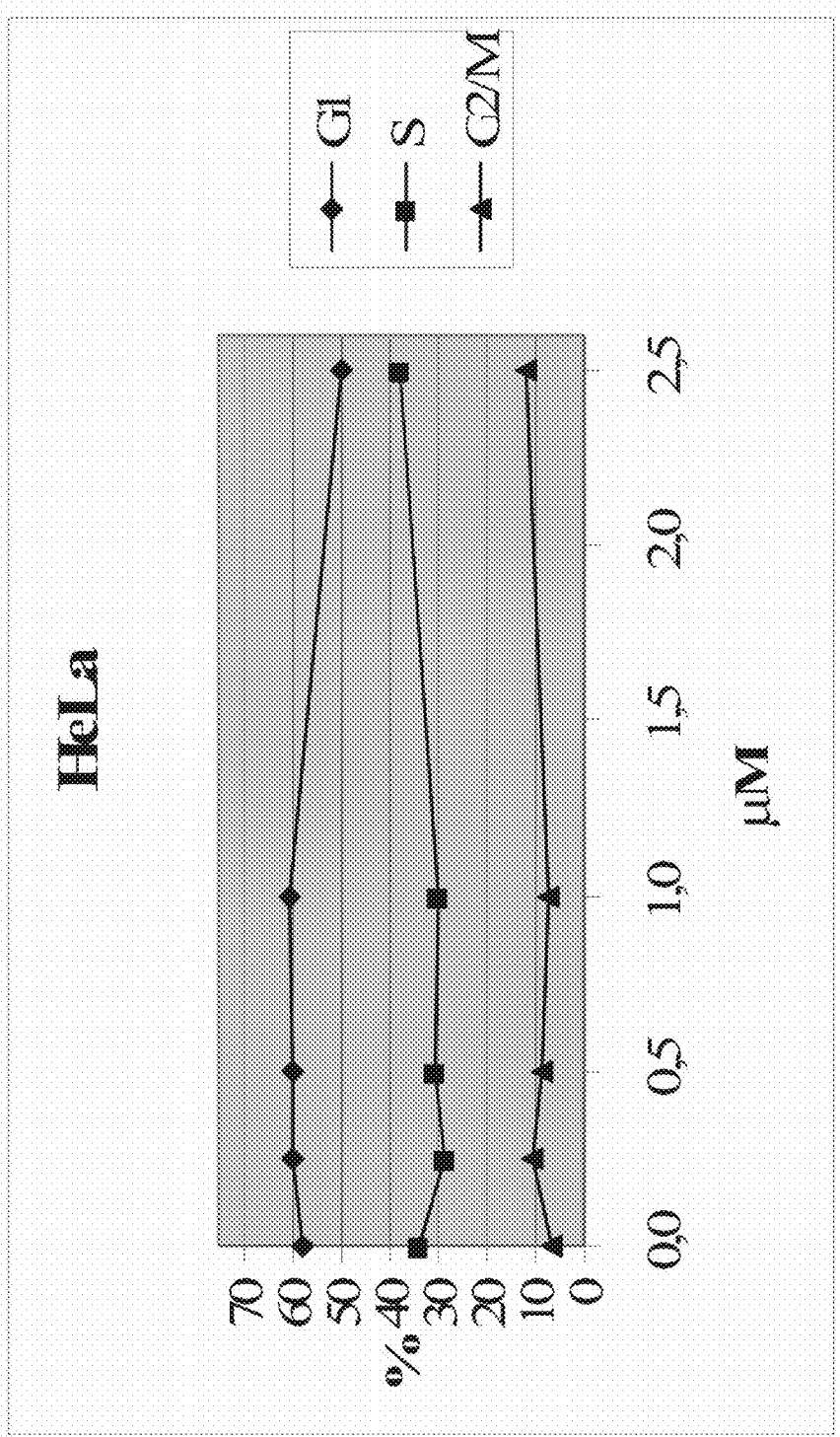
Figure 21:
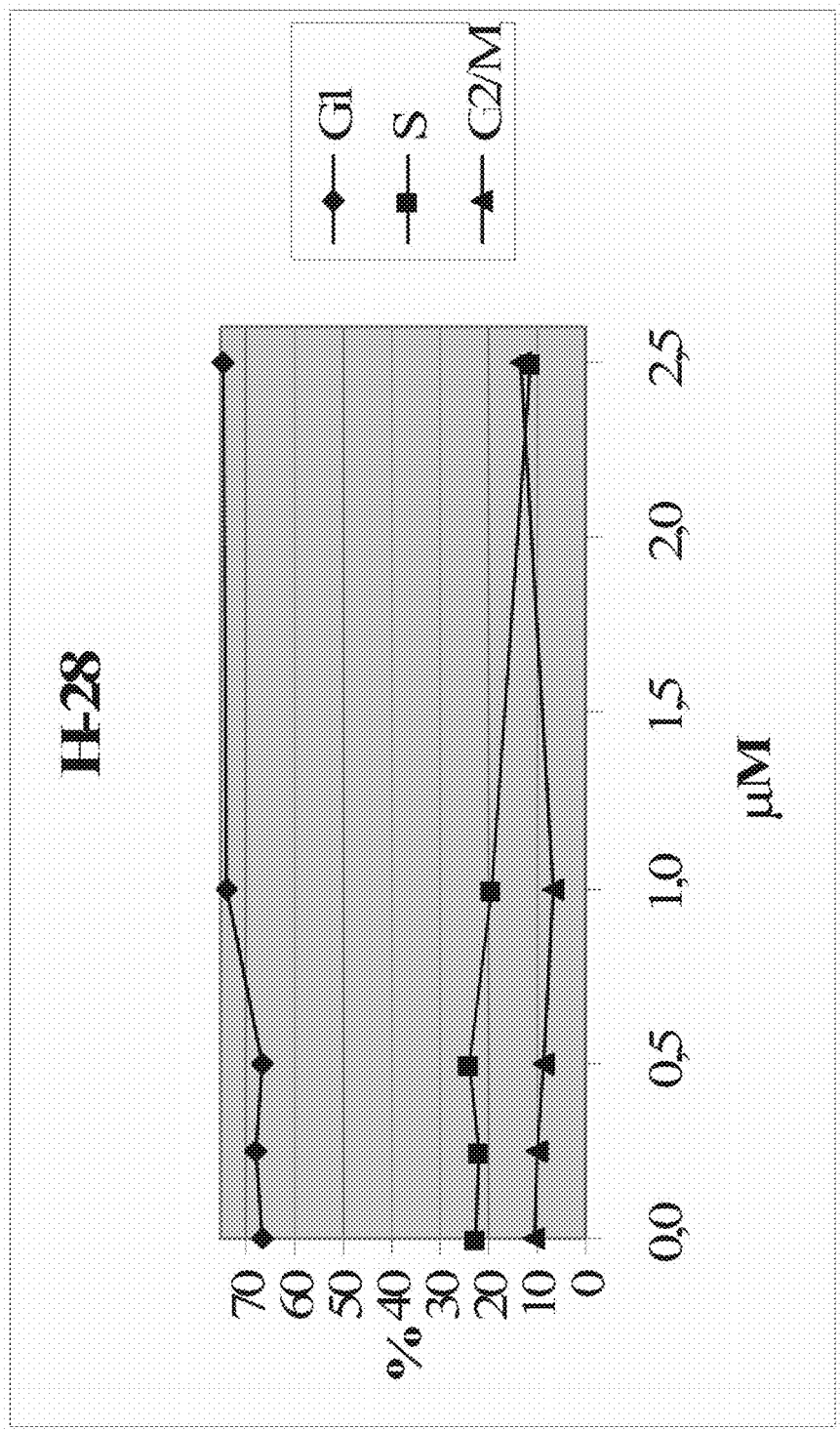
Figure 22:
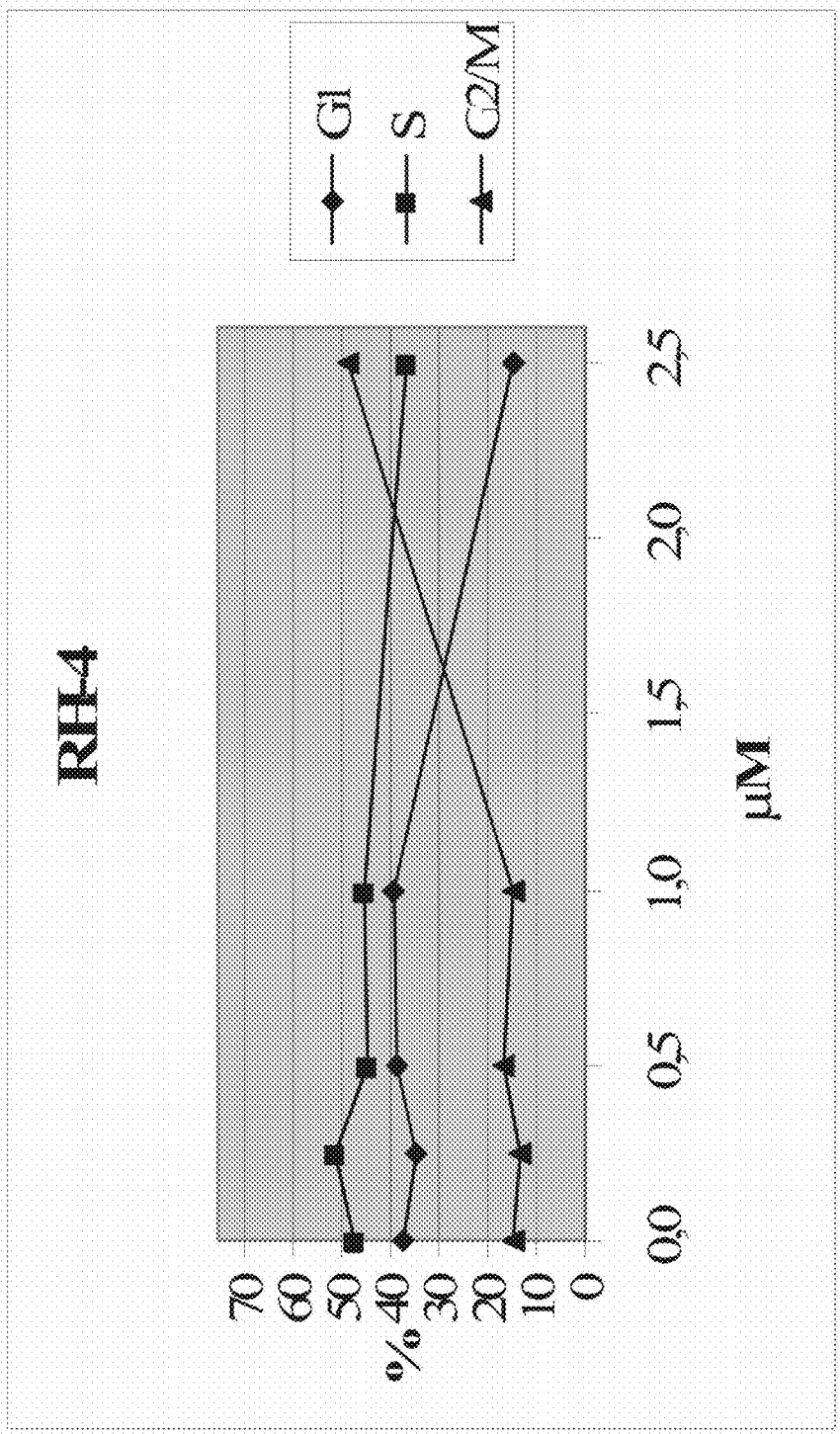
Figure 23:
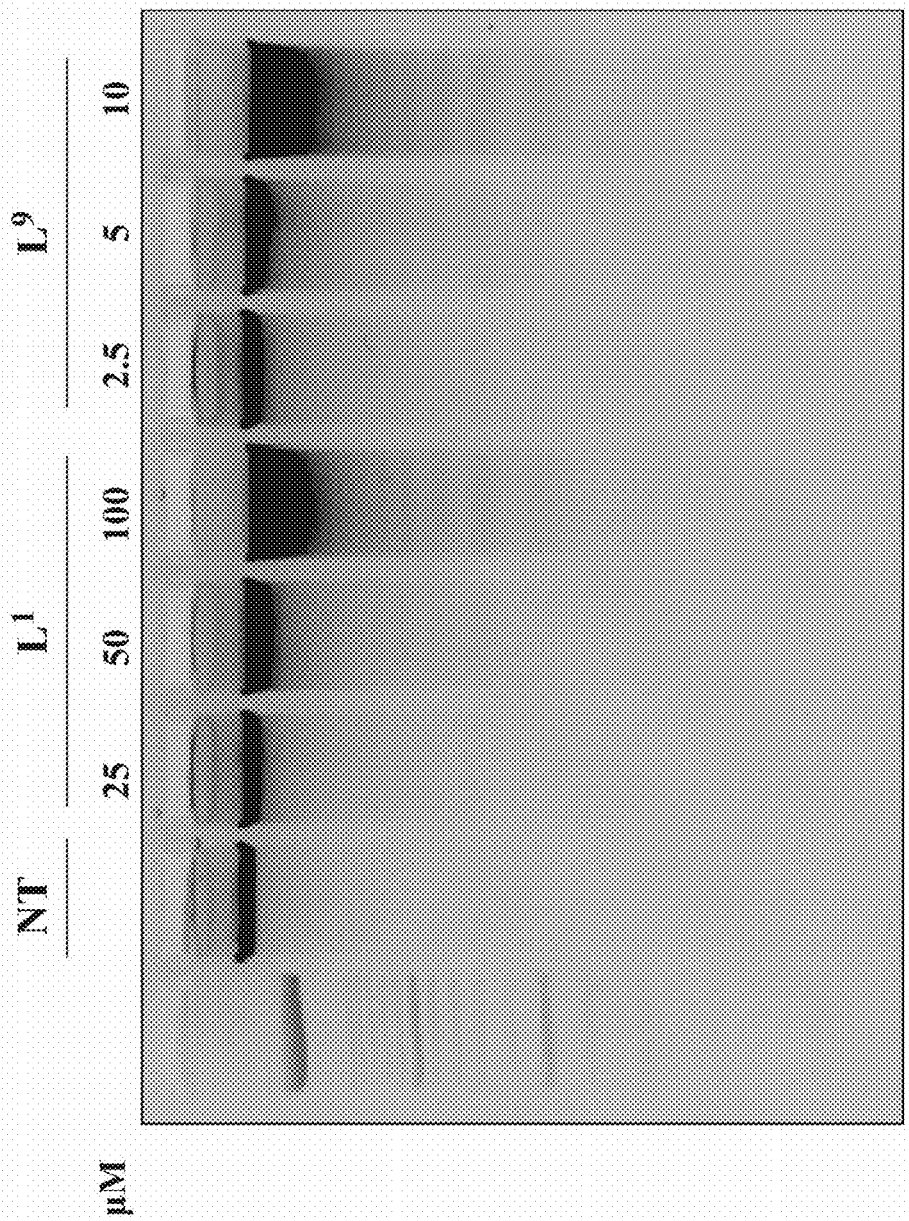
FIG. 23 shows the fragmentation of genomic DNA in U937 cells after treatment with L1 and L9. The cells were treated for 72 hours with L1 and L9 at the concentrations shown in the Figure, the genomic DNA was then extracted, separated on a 2% agarose gel and stained with ethidium bromide.
Figure 24:
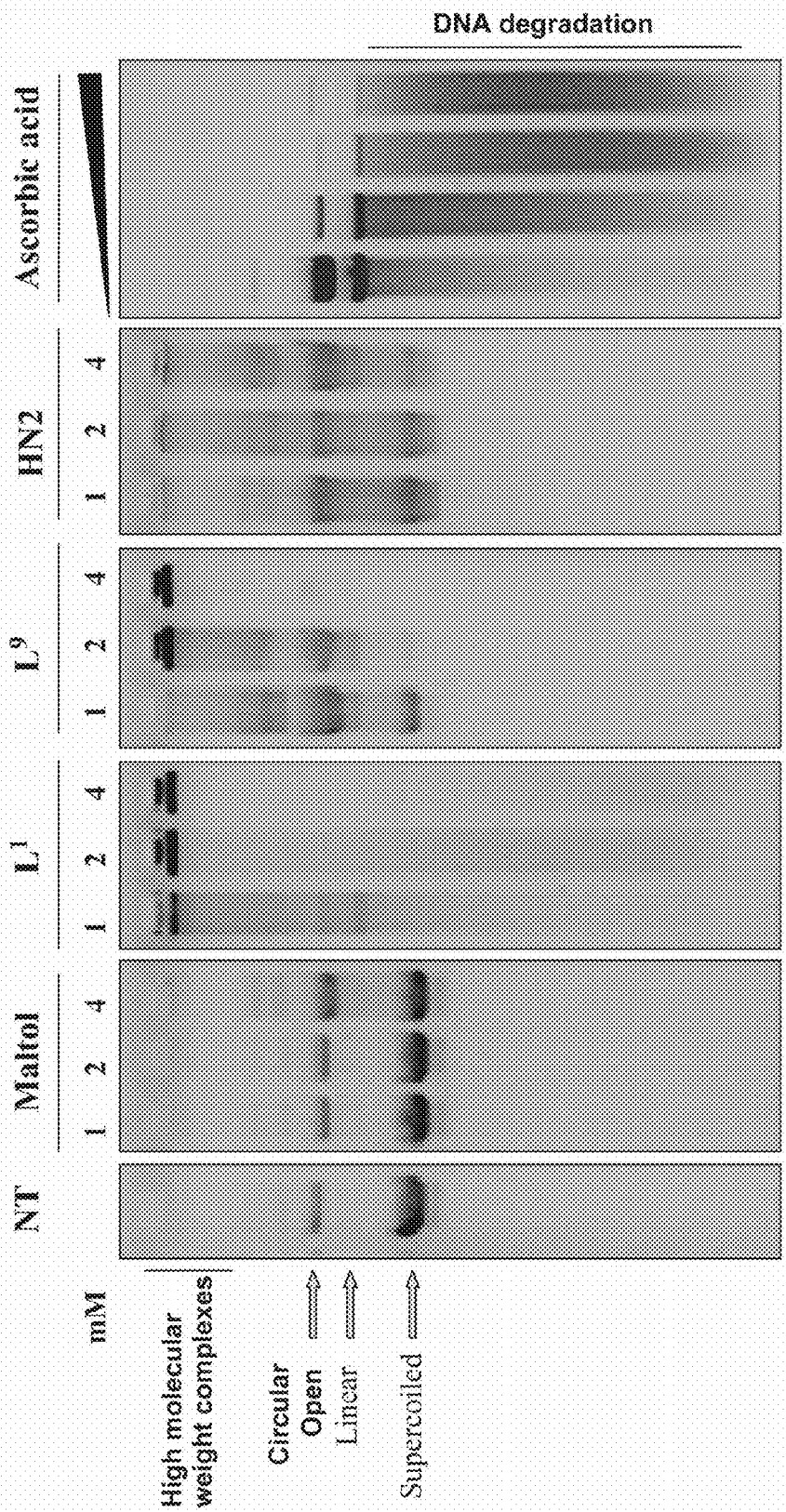
FIGS. 24-26 shows an in vitro assay to evaluate the induction by L1 and L9 of structural alterations of DNA.
Figure 25:
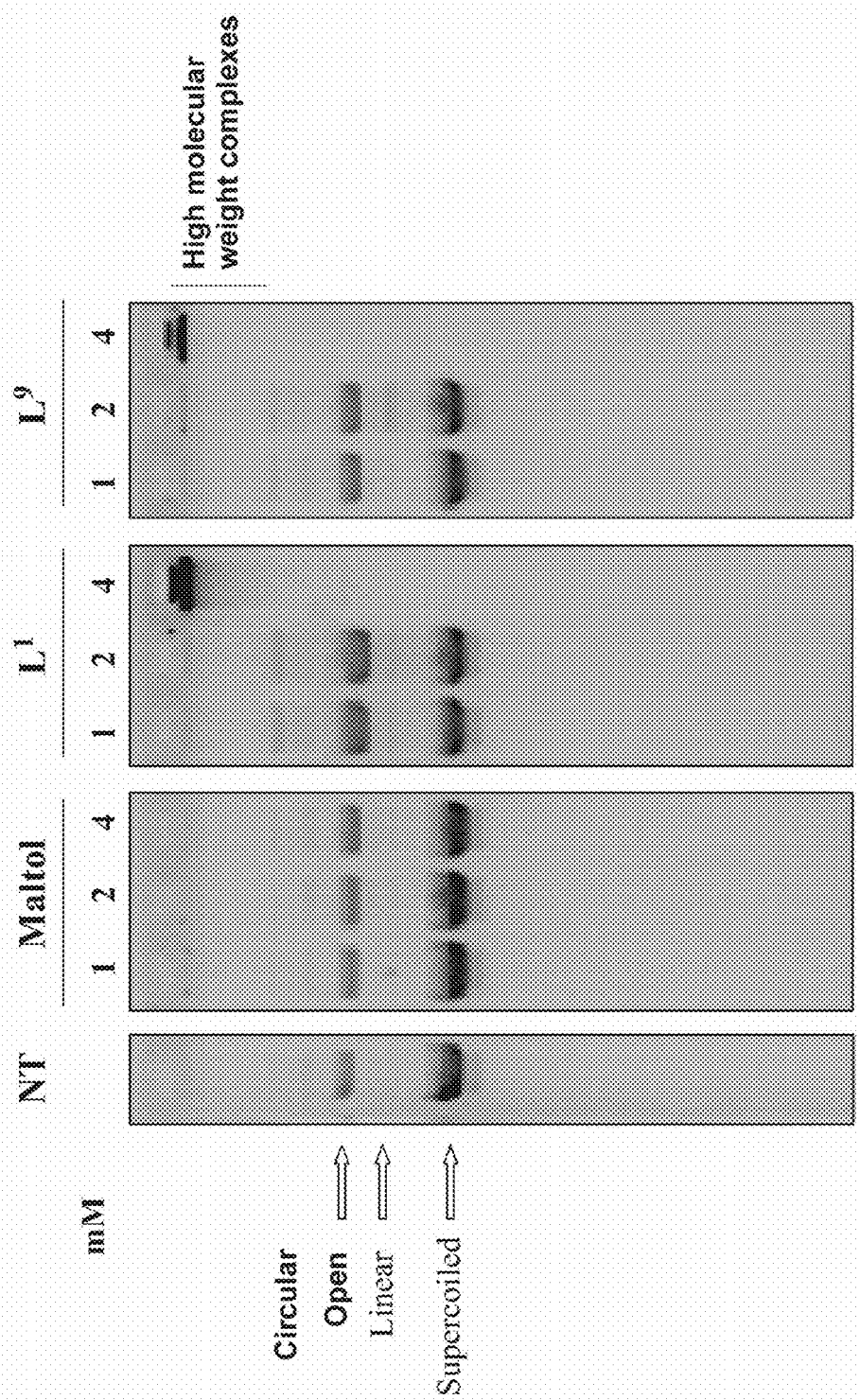
Figure 26:
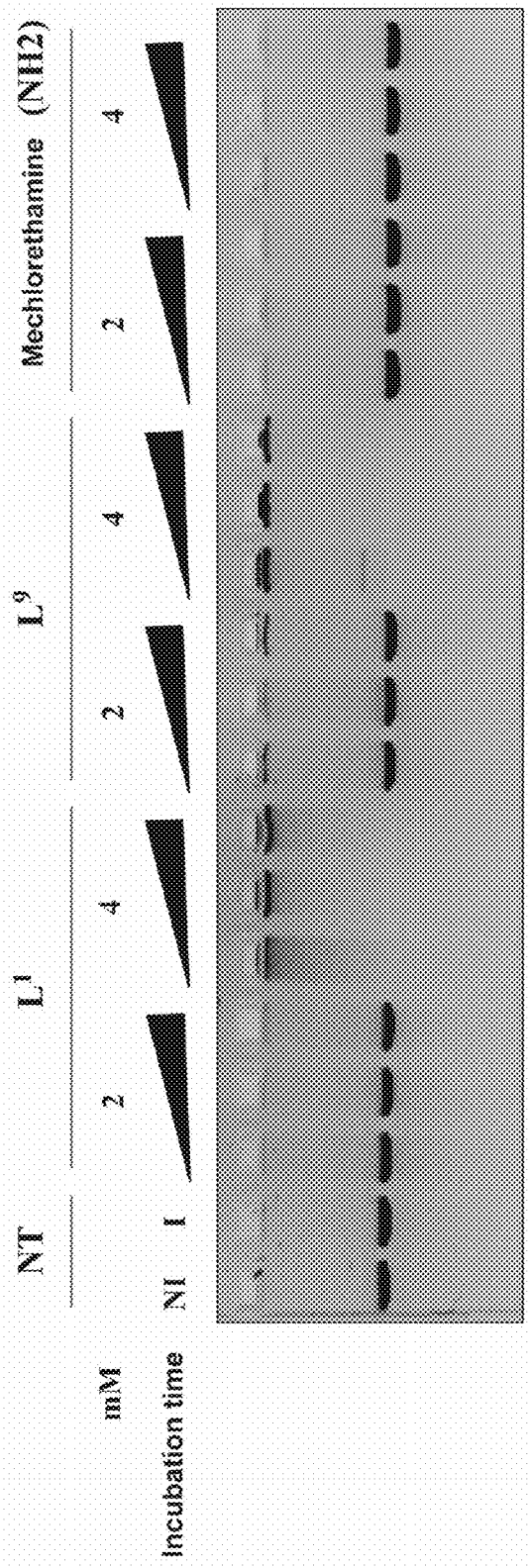

The resulting data show that the treatments with L1 induce apoptosis and interrupt the cell cycle of tumour cells in phase S and G2 in a concentration-dependent manner. Differences have also been identified in the ability to induce apoptosis (FIG. 5) and to interrupt the cell cycle (FIGS. 7-13) in different tumour populations, suggesting a certain specificity of such phenomena. JURKAT and RH-4 cell lines display a severe block in G2 following treatment with L1, while H1-60 and HeLa lines are mainly blocked in phase S and do not show significant increases in the percentage of G2 cells. Also the effects of L9 on apoptosis show a certain specificity (FIG. 14). As regards the modifications of the cell cycle, the tested cell lines are mainly blocked in phase G2 following treatment with L9, except for HeLa and JURKAT cell lines, which stop especially in phase S, and the JL-60 cell line which, together with line H-28, displays a moderate block in phase G1 (FIGS. 15-22).

The induction of apoptosis by compounds L1 and L9 has further been confirmed with the analysis of the fragmentation of the genomic DNA carried out by electrophoresis on an agarose gel. U937 cells treated with L1 (non-treated as a control) at concentrations of 25, 50, 100 μM and L9 at concentrations of 2.5, 5, 10 μM for 72 hours were harvested (about $2\times10^6$ cells), washed with cold 1×PBS and incubated in 2 ml of 1×TBS, 0.5% Tween20, 1 mM EDTA for 30 minutes at +4° C. After being centrifuged at 1200 rpm, for 5 minutes at +4° C., the cells were incubated in 0.5 ml of a solution at 0.1% SDS for 30 minutes at room temperature. The genomic DNA was then extracted by using a QIAquick Gel Extraction Kit (Qiagen, Hilden, Germany), electrophoretically separated by means of a 2% agarose gel and stained with ethidium bromide.

Figure 5:
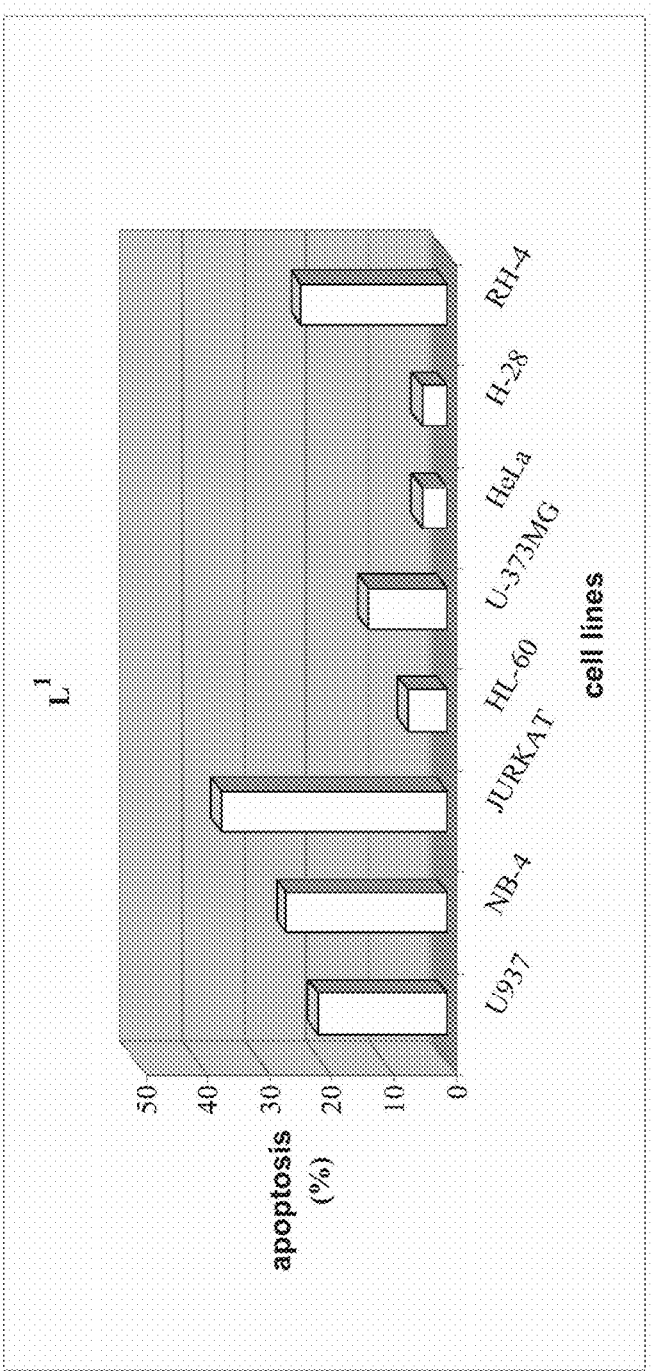
FIGS. 5-22 depict a diagram that shows the modifications induced by L1 and L9 in the percentage of hypodiploid/apoptotic cells and in the progression of the cell cycle in different tumour cell lines monitored by propidium iodide staining and cytofluorimetric analysis.
Figure 6:
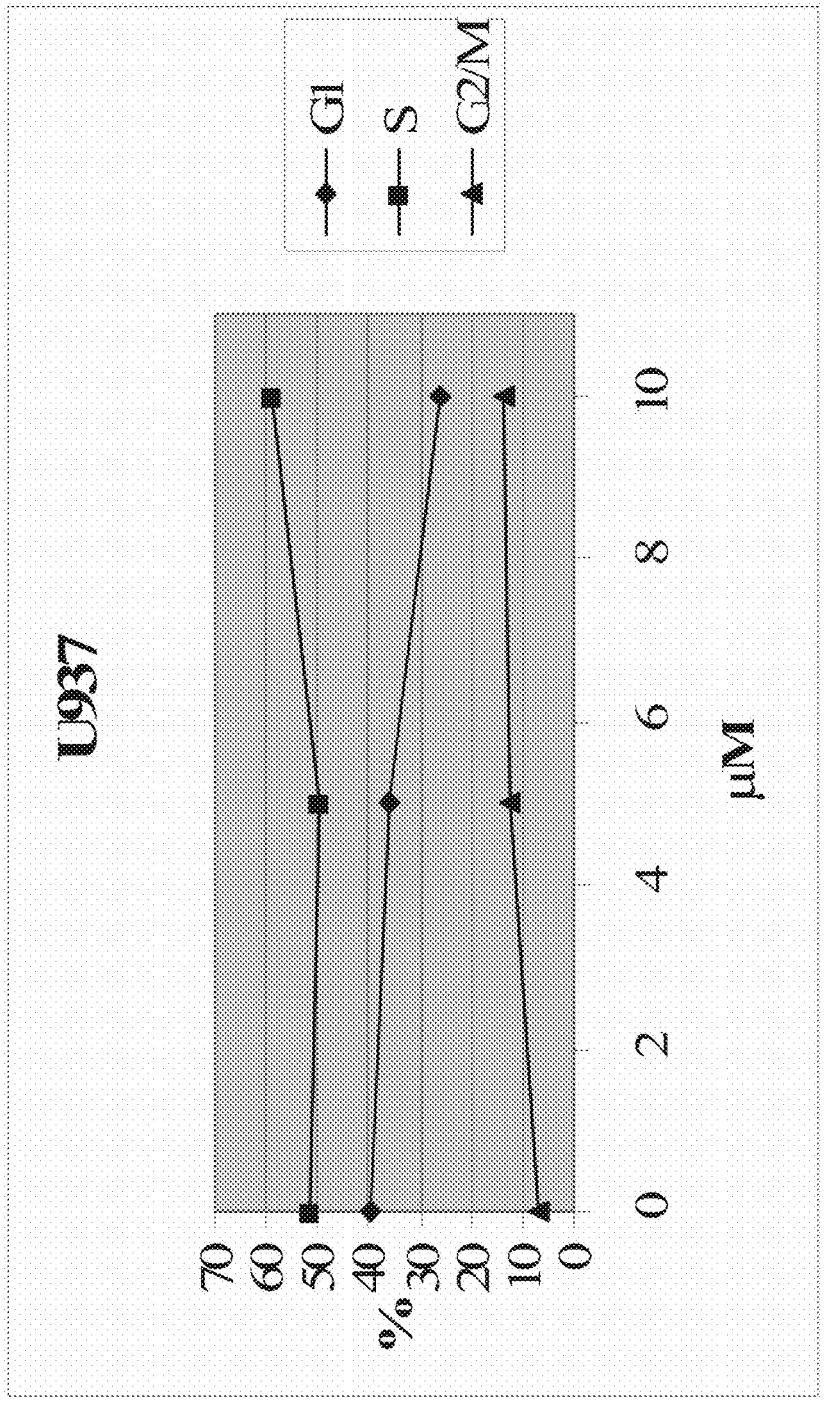
Figure 7:
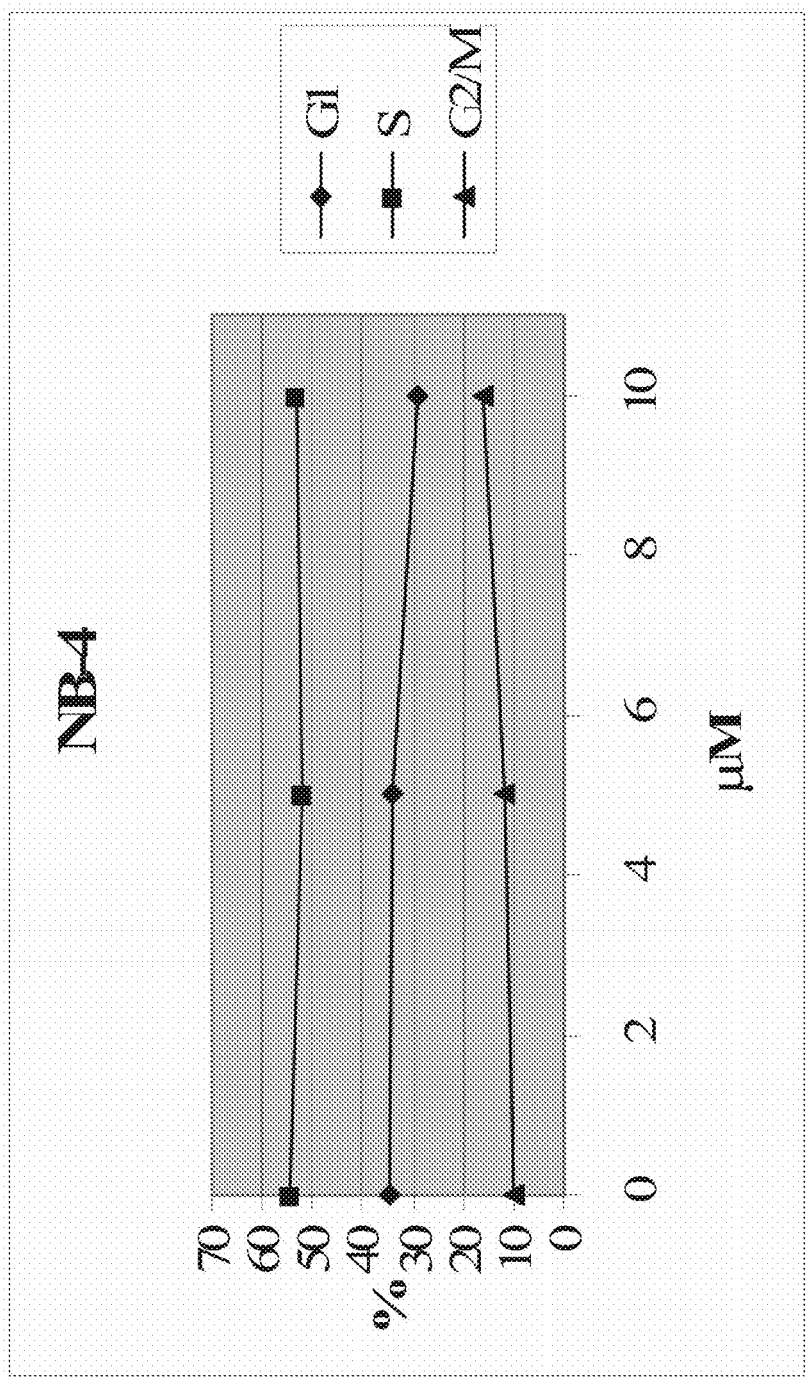
Figure 8:
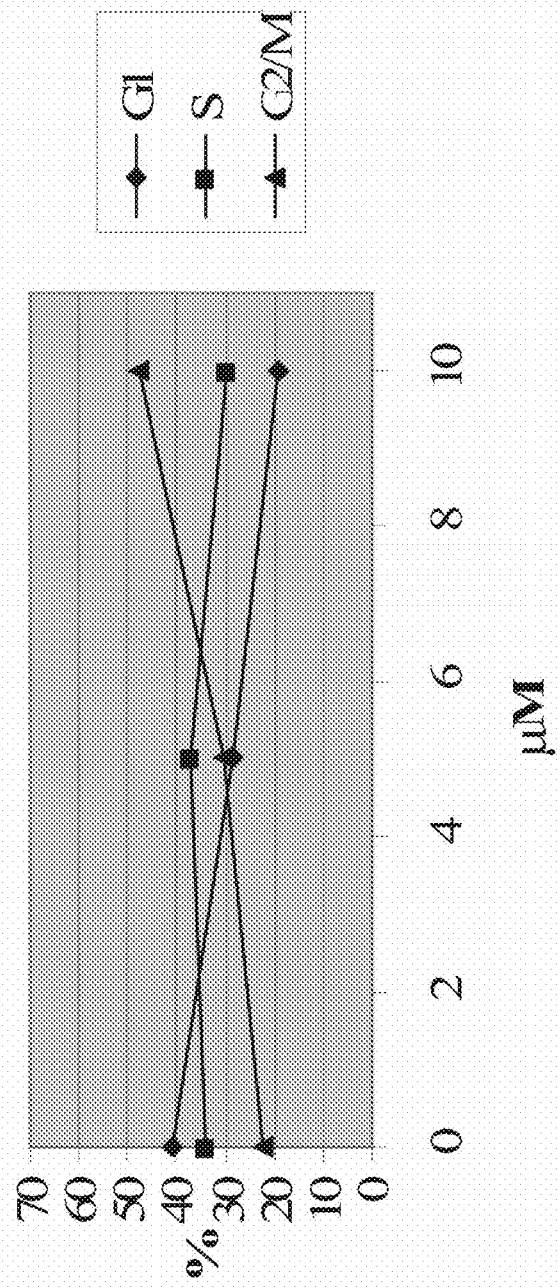
Figure 9:
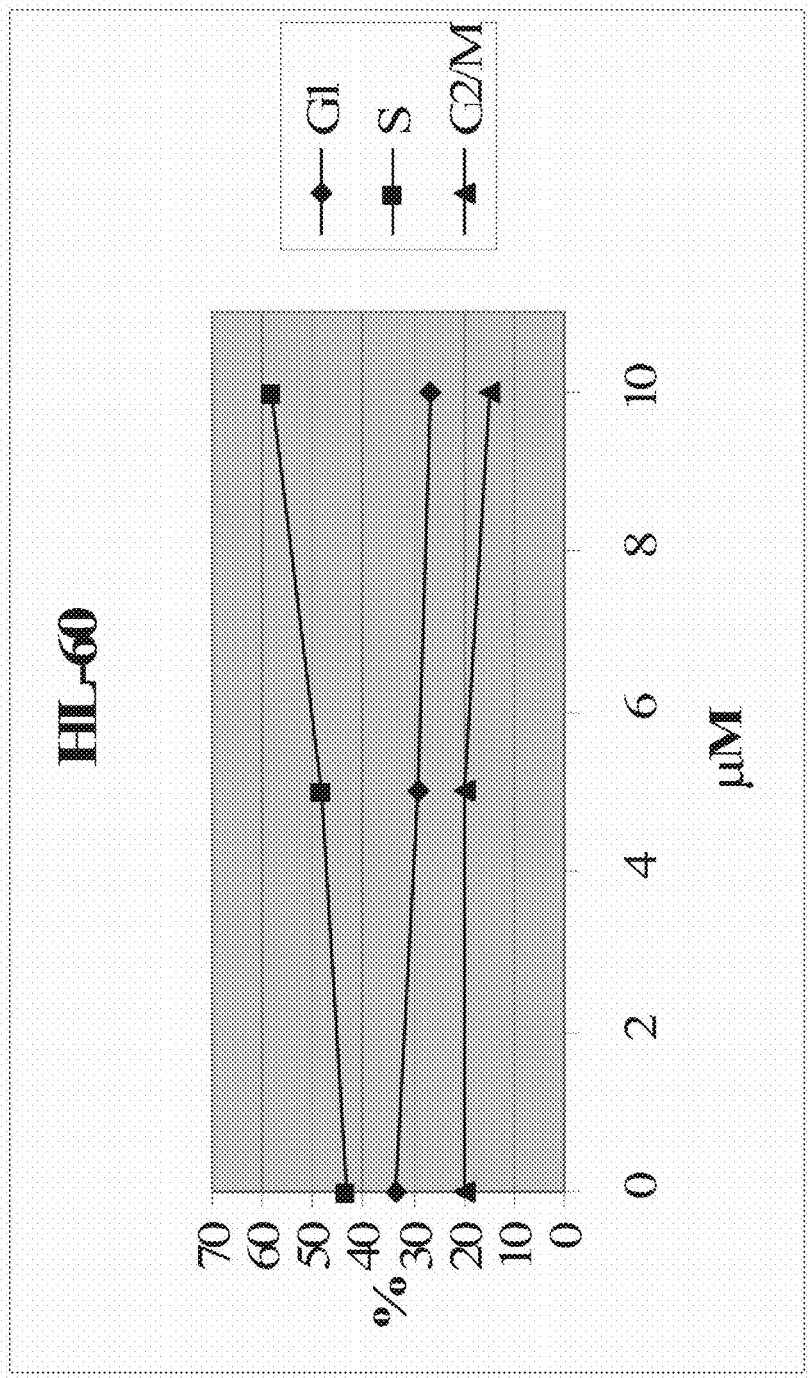
Figure 10:
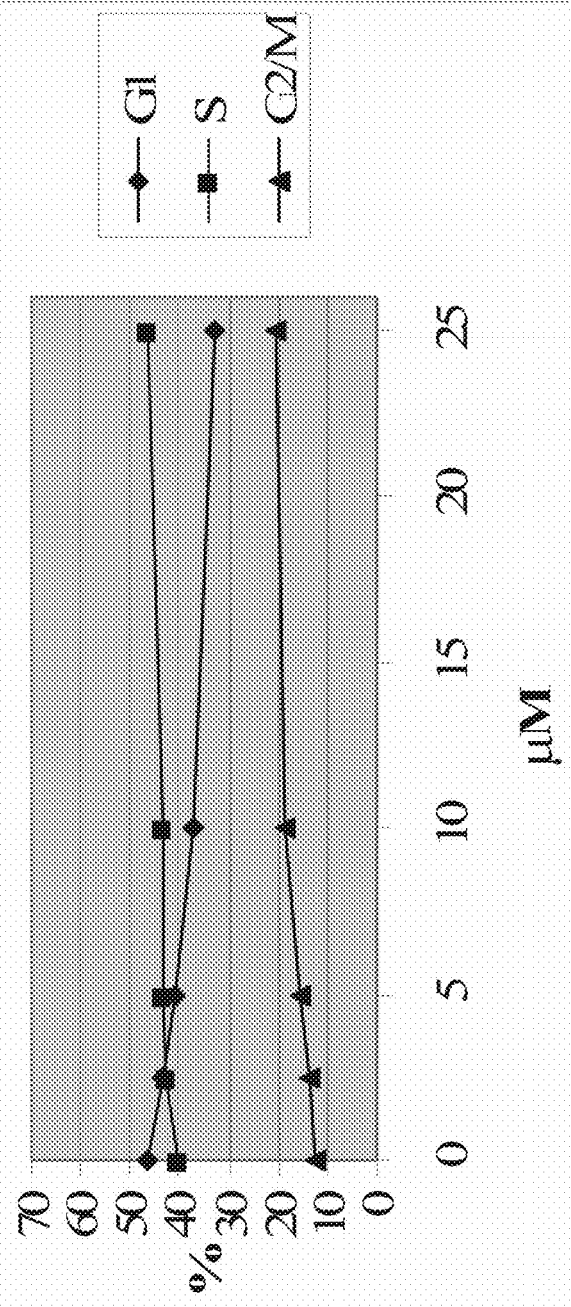
Figure 11:
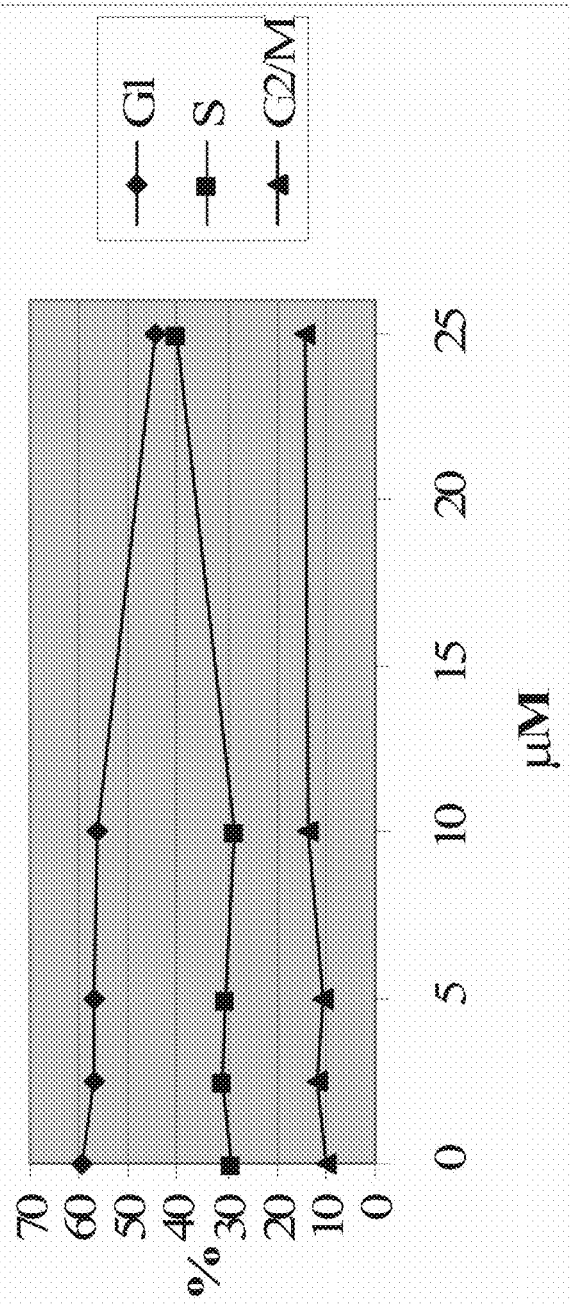
Figure 12:
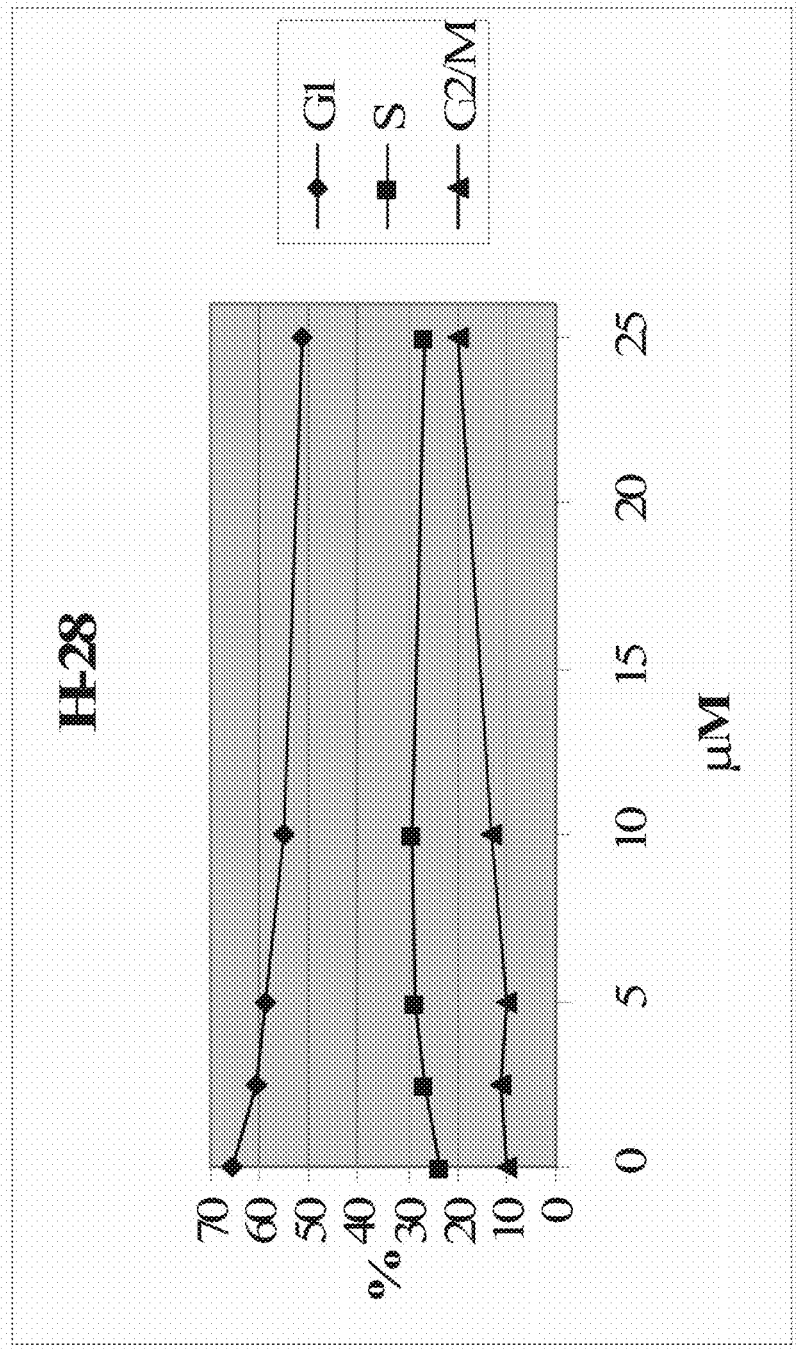
Figure 13:
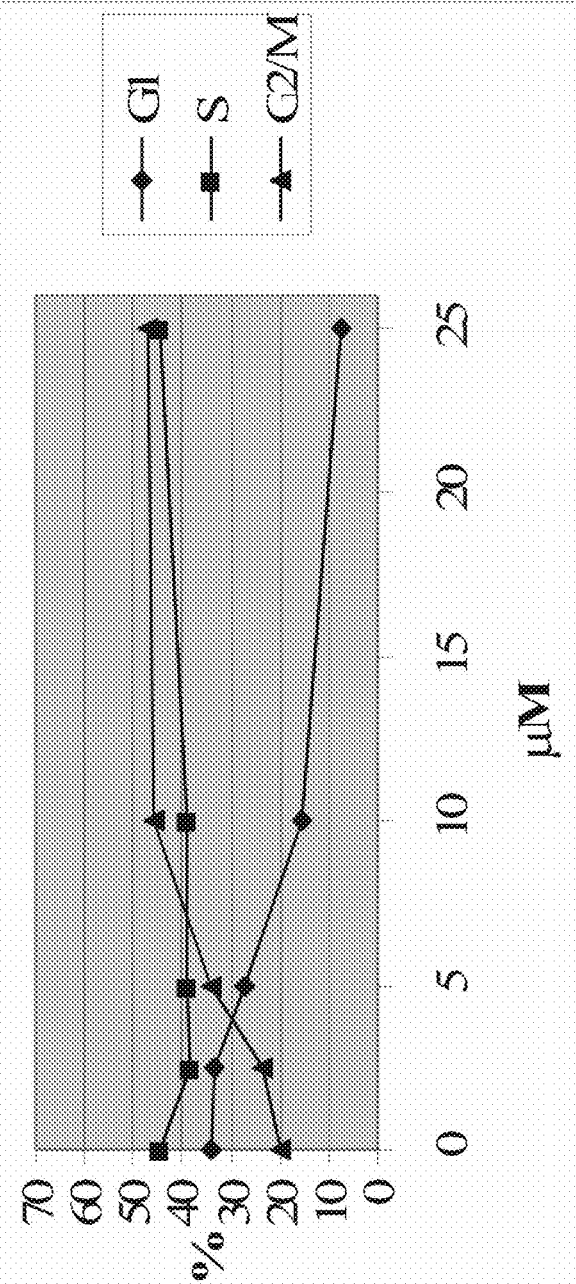

The analysis of genomic DNA allowed to detect a concentration-dependent internucleosomic fragmentation, typical of the programmed death process, both in cells treated with L1 and in cells treated with L9 (FIG. 5).

Example 6

Damage to DNA Induced by Reactive Oxygen Species (ROS) and DNA Intermolecular Crosslinking (ICM) as Mechanisms Underlying the Biological Activity of L1 and L9

The procedure is based on the assumption that double-stranded plasmid DNA, in its original state, substantially has a compact supercoiled configuration characterised by a relatively high electrophoretic mobility. Upon cleaving of single or double stranded DNA, caused by the action of reactive oxygen species (ROS), the supercoiled shape occurs less than respectively an open circular configuration (characterised by a reduced electrophoretic mobility) or the linear shape having an intermediate mobility between that of the other two configurations (Yoshino et al., 1999; Murakami et al., 2007). The effects of these new compounds on the DNA configuration were analysed by incubating 500 ng of plasmid DNA (pLL3.7-7650 Kb) in a circular form or 100 ng in linear form with different concentrations of L1, L9, maltol and mechlorethamine (NH2), at +37° C. for 30, 60, 90 or 120 minutes in 10 mM Tris-HCl, pH 7.4. The treatments were at first carried out in the presence of copper sulphate (CuSO4) at stoichiometric doses with respect to the different concentrations of the tested compounds. Ascorbic acid was used as a control for the damage of the plasmid DNA induced by ROS, as it is a strong reducing agent capable of increasing the pro-oxidising activity of copper ions in vitro (Gaetke et al., 2003). After incubation, the plasmid DNA was analysed by electrophoretic separation on a 0.8% agarose gel and stained with ethidium bromide.

The treatment of the plasmid DNA with compounds L1 and L9 in the presence of copper sulphate, induces an important alteration of the electrophoretic migration of the DNA which results mainly concentrated at the loading well for all the doses tested (FIG. 5). This observation is compatible with a crosslinking activity induced by the testes molecules. In connection to the possibility of generating DNA fragmentation, through the action of ROS, a less efficient tendency to formation of the linear plasmid and open circular species may also be noted (comparing the patterns generated by L1 and L9 with those induced by ascorbic acid and maltol), suggesting a partially ROS-mediated action (also indicated by the occurrence of a "stretch" of smaller fragments) (FIG. 5).

The treatment of the plasmid DNA with mechlorethamine nitrogen mustard, a chemotherapeutic drug having an alkylating action, also known for generating ROS (Bienvenu et al., 1992; Khan et al., 1992), has generated a pattern of plasmid modification very similar to that induced by the treatment with L9, but with the absence of high molecular weight plasmid DNA (fixed in the well).

These observations show that L1 and L9 are capable of at least partially inducing a ROS mediated damage in DNA which depends on copper sulphate and is potentially responsible for the antiproliferative effect monitored in tumour cells. Furthermore, the effect of both molecules is apparent in inducing high molecular weight plasmid species which cannot be targeted electrophoretically and may be correlated to possible intermolecular crosslinking reactions (covalent bonds between different molecules of plasmid DNA) as already disclosed by other authors for other molecules (Pereira et al., 1998; David-Cordonnier et al., 2002).

In order to focus on the hypothetical "cross-linking" activity, similar experiments were carried out in the absence of copper sulphate.

L1 and L9 compounds were found to induce almost exclusively plasmid DNA species having a low electrophoretic mobility and therefore corresponding to a high molecular weight. The monitoring of the formation of high molecular weight species with and without copper sulphate suggests an alkylating activity of L1 and L9 which is presumably responsible for the proved antineoplastic activity, without excluding an at least partial role in the generation of ROS.

Example 7

Evaluation of the Possible Involvement of the Intermediates or Degradation Products Deriving from L1 and L9 in the Corresponding Biological Activities To investigate whether the cytotoxic/inhibitory activity of L1 and L9 on tumour cells could be due to molecular intermediates and/or to products deriving from the degradation of these two molecules, additional treatments were carried out by using the U937 cell model. The cells were plated as previously disclosed and treated for 72 hours with different concentrations of maltol, N-dimethylaminomaltol and tetramethyl ethylendiamine. All of the molecules were diluted in ddH2O and the treatments were repeated every 24 hours. After a 72 hour treatment, cell viability was evaluated by means of an exclusion assay with Trypan Blue.

The resulting data show that the survival of U937 cells is not significantly modified by the treatment with these molecule. This excludes the involvement of molecular intermediates or degradation products in the anti-tumour activity exerted by L1 and L9.

The invention claimed is:
1. Compounds having Formula I:

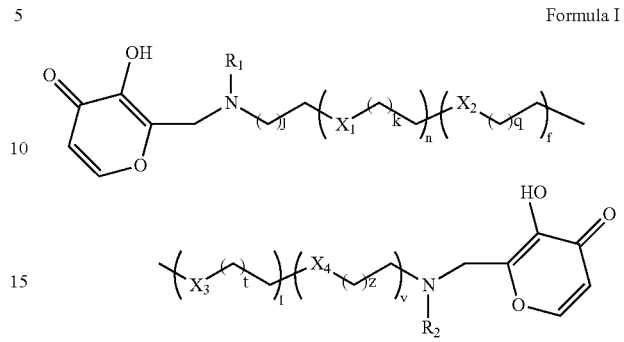

Formula I wherein:
$X_1, X_2, X_3, X_4 = NR_3$, O
$R_3 = H, C_mH_{2m+1}$, m=1, 2, 3, 4, 5, 6
n, f, 1, v=0,1
j, k, q, t, z=1, 2
$R_1, R_2 = C_mH_{2m+1}$, m=1, 2, 3, 4, 5, 6

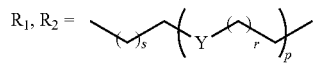

or alternatively form a ring and have the following meaning:
wherein:
$Y = NR_3$, O
$R_3 = H, C_mH_{2m+1}$, m=1, 2, 3, 4, 5, 6
p=0, 1, 2, 3, 4;
s=0, 1, 2
r=1,2
and pharmaceutically acceptable salts thereof.

2. A method of preparing a medicament, comprising:
combining a predetermined dosage of a compound according to claim 1 with at least one of a pharmaceutically acceptable carrier, stabiliser, diluent, excipient and combinations thereof.

3. A method of treating a patient, comprising:
administering an antibiotic comprising a predetermined concentration of a compound according to claim 1.

4. A method of treating a primary tumour, the method comprising:
administering a predetermined dosage of a compound according to claim 1 to the primary tumour to impair cell cycle and programmed cell death;
wherein the primary tumour is at least one of rhabdomyosarcoma, leukaemias and lymphomas.

* * * * *